(12) United States Patent
Gupta et al.

(10) Patent No.: US 10,383,919 B1
(45) Date of Patent: Aug. 20, 2019

(54) FRAGMENTS OF GROWTH HORMONE BINDING PROTEIN

(71) Applicant: The University of the Sciences, Philadelphia, PA (US)

(72) Inventors: Pardeep Gupta, West Chester, PA (US); Snehal Atwe, San Jose, CA (US)

(73) Assignee: The University of the Sciences, Philadelphia, PA (US)

( * ) Notice: Subject to any disclaimer, the term of this patent is extended or adjusted under 35 U.S.C. 154(b) by 0 days.

(21) Appl. No.: 14/293,851

(22) Filed: Jun. 2, 2014

Related U.S. Application Data

(60) Provisional application No. 61/829,655, filed on May 31, 2013.

(51) Int. Cl.
| | |
|---|---|
| *A61K 38/17* | (2006.01) |
| *C07K 14/71* | (2006.01) |
| *A61K 38/27* | (2006.01) |
| *C07K 14/47* | (2006.01) |
| *A61K 38/10* | (2006.01) |

(52) U.S. Cl.
CPC .............. *A61K 38/27* (2013.01); *A61K 38/10* (2013.01); *A61K 38/1709* (2013.01); *C07K 14/47* (2013.01); *C07K 14/71* (2013.01)

(58) Field of Classification Search
None
See application file for complete search history.

(56) References Cited

U.S. PATENT DOCUMENTS

| | | | | |
|---|---|---|---|---|
| 5,646,113 | A | * | 7/1997 | Attie ...................... A61K 38/27 514/11.3 |
| 5,688,763 | A | * | 11/1997 | Hammonds, Jr. ...... G01N 33/74 514/11.3 |
| 2004/0204561 | A1 | | 10/2004 | Ellison |

OTHER PUBLICATIONS

Chenna et al., "Multiple sequence alignment with the Clustal series of programs," *Nucleic Acids Research*, 2003, 31(13):3497-3500.

* cited by examiner

*Primary Examiner* — Christine J Saoud
(74) *Attorney, Agent, or Firm* — Fox Rothschild LLP

(57) ABSTRACT

The present invention features compositions and methods for delivery of growth hormone. We describe compositions comprising fragments of growth hormone-binding protein and, optionally, growth hormone. The compositions can be administered to a patient having a growth disorder or other disorder responsive to growth hormone.

14 Claims, 14 Drawing Sheets
Specification includes a Sequence Listing.

growth hormone receptor isoform 1 precursor [Homo sapiens] NCBI Reference Sequence NP_000154.1 (SEQ ID NO.:12)

Shaded region residues 11-256 disclosed as SEQ ID NO.:14, and residues 19-256 (SEQ ID NO.:11): growth hormone-binding protein

```
  1  mdlwqllltl alagssdafs gseataails rapwslqsvn pglktnsske pkftkcrspe
 61  retfschwtd evhhgtknlg piqlfytrrn tqewtqewke cpdyvsagen scyfnssfts
121  iwipyciklt snggtvdekc fsvdeivqpd ppialnwtll nvsltgihad iqvrweaprn
181  adiqkgwmvl eyelqykevn etkwkmmdpi lttsvpvysl kvdkeyevrv rskqrnsgny
241  gefsevlyvt lpqmsqftce edfyfpwlli iifgifgltv mlfvflfskq qrikmlilpp
301  vpvpkikgid pdllkegkle evntilaihd sykpefhsdd swvefieldi depdektees
361  dtdrllssdh ekshsnlgvk dgdsgrtscc epdiletdfn andihegtse vaqpqrlkge
421  adllcldqkn qnnspyhdac patqqpsviq aeknkpqplp tegaesthqa ahiqlsnpss
481  lsnidfyaqv sditpagsvv lspgqknkag msqcdmhpem vslcqenflm dnayfceada
541  kkcipvaphi kveshiqpsl nqediyitte slttaagrpg tgehvpgsem pvpdytsihi
601  vqspqgliln atalplpdke flsscgyvst dqlnkimp
```

FRAGMENTS OF GROWTH HORMONE BINDING PROTEIN

PRIORITY CLAIM

This application claims the benefit of U.S. provisional application Ser. No. 61/829,655, filed on May 31, 2013. The contents of which is hereby incorporated by reference in its entirety.

FIELD OF THE INVENTION

The present invention relates to methods of treating patients who have a growth disorder and more particularly to methods of making and using polypeptides derived from growth hormone-binding protein to deliver growth hormone to a patient.

BACKGROUND OF THE INVENTION

Growth hormone (GH), also known as somatotropin or somatropin, is a peptide hormone that stimulates growth and differentiation of target tissues. Exogenously administered GH can be an effective treatment for growth disorders in both children and adults. GH is also useful in treating catabolic disorders such as muscle wasting associated with acquired immunodeficiency syndrome (AIDS). Because GH affects a range of tissues, including smooth and cardiac muscle, bone, cartilage, liver, GH may also provide clinical benefit for broader range of disorders including cardiovascular disease, neurological injuries, cerebral palsy and wound healing. However, delivery of GH is challenging. Human GH (hGH) does not withstand the acid environment of the stomach and is typically administered by injection. Moreover, because hGH has a half-life of only about fifteen minutes in the bloodstream, injections must be given daily. These delivery issues can lead to poor compliance and inadequate clinical outcomes. In addition, in healthy subjects, GH is secreted in distinct pulses which are difficult to mimic with exogenously administered GH. There is some evidence to suggest that pulsatile administration may be superior to continuous administration. There is a continuing need for delivery systems that optimize GH dosage and maximize patient compliance.

SUMMARY OF THE INVENTION

The present invention provides compositions comprising a recombinant polypeptide comprising a fragment of a growth hormone binding protein (GHBP) wherein the polypeptide comprises an amino acid sequence selected from the group consisting of: Ser-Pro-Glu-Arg-Glu-Thr-Phe-Ser (SEQ ID NO:1); Arg-Arg-Asn-Thr-Gln-Glu-Trp-Thr-Gln-Glu-Trp-Lys-Glu (SEQ ID NO:2); Arg-Arg-Asn-Thr-Gln-Glu ID NO.: SEQ ID NO:3); Trp-Thr-Gln-Glu-Trp-Lys-Glu (SEQ ID NO:4); Thr-Ser-Ile-Trp-Ile-Pro (SEQ ID NO:5); Val-Asp-Glu-Ile-Val-Gln-Pro-Asp (SEQ ID NO.: SEQ ID NO:6); Thr-Ser-Ile-Trp-Ile-Pro-Tyr-Cys-Ile-Gly-Lys-Cys-Phe-Ser-Val-Asp-Glu-Ile-Val-Gln-Pro-Asp (SEQ ID NO:7); Thr-Ser-Ile-Trp-Ile-Pro-Tyr-Gly-Ser-Val-Asp-Gludle-Val-Gln-Pro-Asp (SEQ ID NO:8); Lys-Val-Asp-Lys-Glu-Tyr-Glu (SEQ ID NO:9); and Arg-Val-Arg-Ser-Lys-Gln-Arg (SEQ ID NO:10). In some embodiments, the polypeptide can comprise an amino acid sequence that is at least 80% identical to SEQ ID NOs: 1-10, including, for example, at least 80%, 85%, 90%, 91%, 92%, 93%, 94%, 95%, 96%, 97%, 98%, and/or 99%. The polypeptides can be formulated as a pharmaceutical composition comprising a pharmaceutically acceptable carrier, for example, a liposome, nanoparticle of carrier protein. In some embodiments, the compositions comprises growth hormone. Also provided are kits comprising one or more of the polypeptides of SEQ ID NOs: 1-10, instructions for use, and optionally, a growth hormone. Also provided are methods of treating a subject who has a growth disorder, the method comprising administering a therapeutically effective amount of a pharmaceutical composition comprising fragment of a growth hormone binding protein and optionally, a growth hormone.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 13 shows the sequence for the growth hormone receptor isoform 1, residues 1-638 (SEQ ID NO:12). The shaded portion of the sequence (residues 11-256) is SEQ ID NO:14 and residues 19-256 correspond to SEQ ID NO:11.

Figure 1:
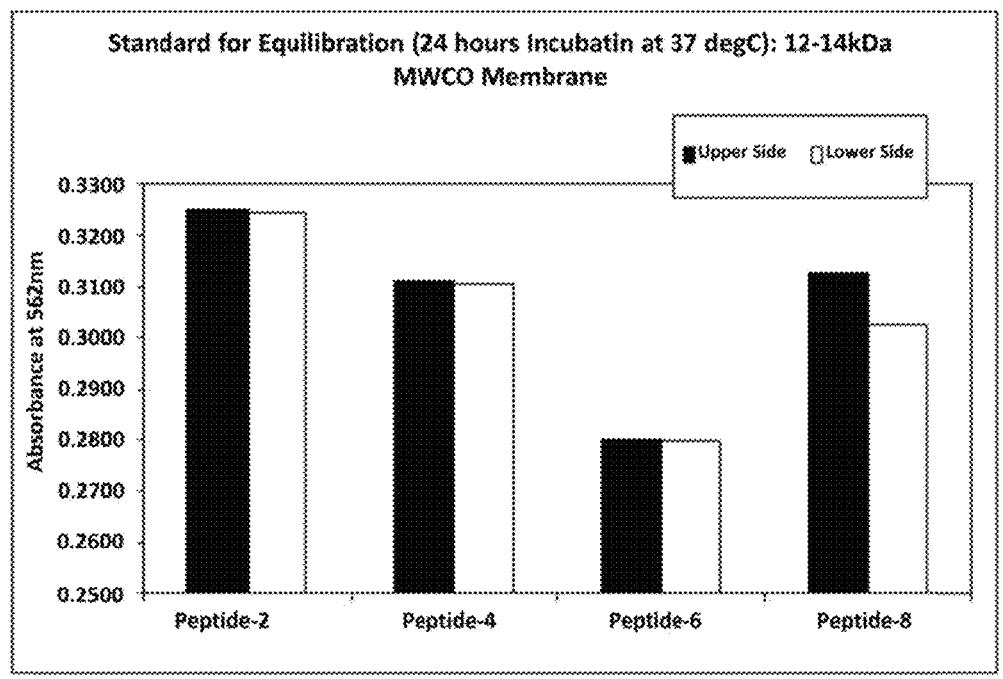
FIG. 1 is a graph depicting the results of an analysis of the effect of a 12-14 kDA MWCO membrane on diffusion of HGBP peptides of SEQ ID NO.:2, SEQ ID NO.:4, SEQ ID NO.:6, and SEQ ID NO.:8.

The instant application contains a Sequence Listing which has been submitted electronically in ASCII format and is hereby incorporated by reference in its entirety. Said ASCII copy, created on May 28, 2014, is named B3497-00172_SL.txt and is 17,570 bytes in size.

DETAILED DESCRIPTION OF THE PREFERRED EMBODIMENT

The present invention is based in part in the inventors' discovery that particular fragments of human growth hormone-binding protein (hGHBP) or human growth hormone receptor (hGHR) specifically bind human growth hormone (hGH). Accordingly, the invention features compositions that can be used to deliver growth hormone, for example, human growth hormone, to a subject. The compositions are useful for the treatment of a wide range of conditions in which GH is implicated, including growth disorders, cardiovascular disease, neurological injuries, cerebral palsy and wound healing.

GH exerts its physiological effects through binding to growth hormone receptor. Human growth hormone receptor (GHR) is a 620 amino acid protein and belongs to GH/Prolactin hematopoetic Class I cytokine receptor family. GHR is highly conserved evolutionarily, with the monkey, rabbit, pig, sheep, cow, mouse, rat, and chicken amino acid sequences having 94%, 84%, 83%, 81%, 76%, 70%, 69% and 50% sequence identity to the human isoform 1 sequence.

The 246 amino acid extracellular domain of GHR is shed into the circulation by proteolytic cleavage by TACE (TNF-alpha converting enzyme) to generate a high affinity binding 238 amino acid growth hormone binding protein (GHBP). The high affinity GHBP is an integral part of the growth hormone (GH)-insulin-like growth factor axis. Depending on the species, it is either a cleavage product of the GHR or a splice variant of the Ghr gene. GHBP modulates GH action through both inhibitory and enhancing mechanisms. GHBP can act as an agonist/antagonist depending on levels of GH, GHR turnover, post-receptor regulation of GHR and plasma GHBP levels. About 5-20% circulating GH binds to low affinity GHBP.

Removal of residues 7-28 in GHBP do not affect binding its ability to bind GH. Eleven residues have been reported to contribute to hGH binding (Arg43, Glu44, Ile103, Trp104, 11e105, Pro106, Asp126, Glu127, Asp164, Ile165 and Trp169). Many of these play indirect structural roles by supporting and positioning Trp104 and Trp169 for binding. The interface is composed mainly of side-chain interactions participating in aliphatic-aromatic stacking interactions. Binding surface on hGHbp is relatively "soft" and the binding determinants are on loops; in case of hGH they are on the loops and the surface is relatively "hard". The main functional epitope is hydrophobic framed by polar residues to permit binding of only "correct" partners. The binding regions include four segments in the cysteine-rich domain of the hGHbp. These segments include-Thr101 to Pro106; Va1125 to Asp132; Arg70 to Glu82; and—Glu42 to Glu44. There is electrostatic complementarity between an electropositive binding epitope on hGH and an electronegative epitope on hGHbp. Of the 10 charged-to-alanine substitutions in the hGHBP that have been shown to reduce binding affinity 7 are acidic residues. On the other hand on hGH 3 of the 5 disruptive binding sites are basic residues and none are acidic residues.

While we believe we understand certain events that occur upon administration of compositions comprising GHBP fragments alone or in combination with GH, the compositions of the present invention are not limited to those that work by affecting any particular cellular mechanism. Our working hypothesis is that the polypeptides of the invention specifically bind to GH and can prolong the half-life of circulating GH.

Compositions

Polypeptides:

The compositions include polypeptides derived from a GHBP, which may be either a GH Receptor (GHR) or the circulating, soluble form of extracelluar domain of the GH Receptor known as GHBP and/or biologically active variants thereof. A polypeptide that has a sequence that is identical to a portion of a GHBP sequence and that functions (e.g., for one or more of the purposes described herein) is a fragment of a GHBP. The GH Receptor includes the GHBP sequence and one or more of the polypeptides described herein may lie partially or wholly within GHBP sequence. A polypeptide that has a sequence that differs to a certain limited extent from a sequence that is found in a naturally occurring GHBP and that retains the ability to function (e.g., retains sufficient activity to be used for one or more of the purposes described herein) is a biologically active variant of a GHBP. We tend to use the terms "GH Receptor" and "GHBP" to refer to full-length, naturally-occurring GHBP proteins, and we tend to use the terms "polypeptide" and "peptide" when referring to fragments thereof (i.e., to fragments of GHBP) and biologically active variants thereof. Because the polypeptides or peptides can have a sequence that is identical to a sequence found in GHBP, the polypeptides or peptides are derived from fragments of a GHBP.

The compositions including fragments of a GHBP and/or biologically active variants thereof can be formulated in various ways and can include pharmaceutically acceptable carriers. For ease of reading, we do not repeat the phrase "and/or biologically active variants thereof" after every reference to a fragment of a GHBP. It is to be understood that where a fragment of a GHBP is useful, a variant of the polypeptide that has comparable biological activity (e.g., sufficient activity to be used for one or more of the purposes described herein (e.g., for the purpose for which one would have used a fragment of a GHBP)) is also useful. The fragment of a GHBP can be a fragment of any isoform of GHBP, for example, isoform 1, 2, 3, or 4.

The NCBI reference sequence for hGH Receptor precursor isoform 1 can be found at Genbank under accession number NP_000154.1. public GI:4503993. We refer to this sequence as SEQ ID NO:12. The corresponding cDNA sequence is found at Genbank under accession number NM_000163.4. public GI:335057506. We refer to this sequence as SEQ ID NO:13. The mature 620 amino acid form of hGHR (SEQ ID NO:12) lacks the 18 amino acid signal peptide at the C-terminus (i.e., amino acids 1-18.) The 238 amino acid circulating soluble hGHBP form, which we refer to as SEQ ID NO:11, extends from amino acid 19-256 of the hGHR (SEQ ID SEQ ID NO:12). SEQ ID NO:14, shaded in FIG. 13, which extends from amino acid 11-256 of the hGHR (SEQ ID NO:12) is also included herein.

Accordingly, the invention features physiologically acceptable compositions and concentrated stocks of fragments of a GHBP and methods by which those fragments can be prepared and formulated for administration to a patient diagnosed as having, for example, a growth disorder. While the sequences of the present polypeptides can vary, useful polypeptides can include fragments of SEQ ID NO:11 (hGHBP), SEQ ID NO:14 or SEQ ID NO:12 (HGHR). The polypeptides can include or consist of an amino acid sequence of a GHBP that is naturally expressed in a mammalian cell (e.g., a human cell). A biologically active variant can include, for example, an amino acid sequence that differs from a wild-type fragment of a GHBP by virtue of containing one or more conservative amino acid substitutions. In some embodiments, at least 50% of the amino acid residues of the variant are identical to residues in the corresponding wildtype fragment of a GHBP. Biologically active variants can also include amino acid sequences that differ from a wild-type fragment of a GHBP by virtue of non-conservative amino acid substitutions, additions, and/or deletions. These variants are described in more detail below.

More specifically, the fragments of a GHBP can have, or can include, a sequence of amino acid residues conforming to the amino acid sequences below:
Ser-Pro-Glu-Arg-Glu-Thr-Phe-Ser (SEQ ID NO:1);
Arg-Arg-Asn-Thr-Gln-Glu-Trp-Thr-Gln-Glu-Trp-Lys-Glu (SEQ ID NO:2);
Arg-Arg-Asn-Thr-Gln-Glu (SEQ ID NO:3);
Trp-Thr-Gln-Glu-Trp-Lys-Glu (SEQ ID NO:4);
Thr-Ser-Ile-Trp-Ile-Pro (SEQ ID NO:5);
Val-Asp-Glu-Ile-Val-Gln-Pro-Asp (SEQ ID NO:6);
Thr-Ser-Ile-Trp-Ile-Pro-Tyr-Cys-Ile-Gly-Lys-Cys-Phe-Ser-Val-Asp-Glu-Ile-Val-Gln-Pro-Asp (SEQ ID NO:7);
Thr-Ser-Ile-Trp-Ile-Pro-Tyr-Gly-Ser-Val-Asp-Gludle-Val-Gln-Pro-Asp (SEQ ID NO:8);
Lys-Val-Asp-Lys-Glu-Tyr-Glu (SEQ ID NO:9); and
Arg-Val-Arg-Ser-Lys-Gln-Arg (SEQ ID NO:10).

We refer to the amino acid-based compositions of the invention as "polypeptides" to convey that they are linear polymers of amino acid residues, and to help distinguish them from full-length proteins. While the content of the polypeptides of the invention can vary, none of them are full-length, naturally-occurring GHBPs. We have stated that a polypeptide of the invention can "constitute" or "include" a fragment of a GHBP, and the invention encompasses polypeptides that constitute or include fragments of a GHBP or biologically active variants thereof. It will be understood that the polypeptides can therefore include only a fragment of a GHBP (or a biologically active variant thereof) but may include additional residues as well. The polypeptides of the invention can vary in length. For example, the polypeptides can be 8-40 (e.g., 12, 14, 16, 18, or 20) amino acids long or longer (e.g., up to about 40 residues).

A polypeptide of the invention can have an amino acid sequence conforming to any of the following:
Ser-Pro-Glu-Arg-Glu-Thr-Phe-Ser (SEQ ID NO:1);
Arg-Arg-Asn-Thr-Gln-Glu-Trp-Thr-Gln-Glu-Trp-Lys-Glu (SEQ ID NO:2);
Arg-Arg-Asn-Thr-Gln-Glu (SEQ ID NO:3);
Trp-Thr-Gln-Glu-Trp-Lys-Glu (SEQ ID NO:4);
Thr-Ser-Ile-Trp-Ile-Pro (SEQ ID NO:5);
Val-Asp-Glu-Ile-Val-Gln-Pro-Asp (SEQ ID NO:6);
Thr-Ser-Ile-Trp-Ile-Pro-Tyr-Cys-Ile-Gly-Lys-Cys-Phe-Ser-Val-Asp-Glu-Ile-Val-Gln-Pro-Asp (SEQ ID NO:7);
Thr-Ser-Ile-Trp-Ile-Pro-Tyr-Gly-Ser-Val-Asp-Gludle-Val-Gln-Pro-Asp SEQ ID NO:8);
Lys-Val-Asp-Lys-Glu-Tyr-Glu (SEQ ID NO:9); and
Arg-Val-Arg-Ser-Lys-Gln-Arg (SEQ ID NO:10).

For the sake of added clarity, the polypeptides of the invention exclude naturally occurring full-length GHBPs, but such full-length GHBPs may be included in the pharmaceutical compositions described herein, modified as described herein (e.g., amidated), and used together with the presently described polypeptides in any method or embodiment of the present invention.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a fragment of a GHBP can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

One or more of the amino acid residues in a biologically active variant may be a non-naturally occurring amino acid residue. Naturally, occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (for example, a site is currently maintained by the California Institute of Technology and displays structures of non-natural amino acids that have been successfully incorporated into functional proteins). Non-natural amino acid residues and amino acid derivatives listed in U.S. Application No. 20040204561 (see 910042, for example) can also be used. Alternatively, or in addition, one or more of the amino acid residues in a biologically active variant can be a naturally occurring residue that differs from the naturally occurring residue found in the corresponding position in a wild type GHBP sequence. In other words, biologically active variants can include one or more amino acid substitutions, and these may be substitutions with naturally or non-naturally occurring residues (or a combination thereof). We may refer to a substitution, addition, or deletion of amino acid residues as a mutation of the wild type sequence. As noted, the substitution can replace a naturally occurring amino acid residue with a non-naturally occurring residue or just a different naturally occurring residue. Further, the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a GHBP can be characterized in terms of the extent to which their sequence is similar to or identical to the corresponding fragment of the GHBP. For example, the sequence of a biologically active variant can be at least or about 60% identical to corresponding residues in a wild type GHBP. For example, a biologically active variant of a GHBP polypeptide can have an amino acid sequence with at least or about 60% sequence identity (e.g., at least or about 65%, 70%, 75%, 80%, 85%, 90%, 95%, 97%, 98%, or 99% sequence identity) to a GHBP (e.g., to the amino acid sequence set forth in SEQ ID NO:11 or to another polypeptide as described herein (e.g., a polypeptide represented by, for example, SEQ ID NOs:1-10, SEQ ID NO:14) or to a homolog or ortholog thereof).

A biologically active variant of a GHBP polypeptide will retain sufficient biological activity to be useful in the present methods. The biological activity can be assessed in ways known to one of ordinary skill in the art and includes, without limitation, equilibrium dialysis, solution binding assays, or plasma GH levels. Biologically active variants can be identified, for example, by comparing the relative activities of the variant polypeptide with that of an active fragment of a GHBP. The assays can include an unrelated control polypeptide (e.g., one could include in any given assay a peptide that has the same amino acid content randomly arranged, as well as a vehicle-only control). Some biologically active variants may even have greater biological activity than the cognate, naturally occurring fragment or a full-length GHBP. More specifically, a biologically active variant can have at least or about 30%, 40%, 50%, 60%, 70%, 80%, 90%, 95%, 98%, or more of the biological activity of the native form polypeptide.

The methods that can be used to assess activity include in silico analyses, in vitro assays, cell-based assays and whole animal, in vivo, model systems. These assays can be configured to test the effect of any given fragment of a GHBP, or a variant thereof, on a variety of processes, including for example, receptor mediated signaling, IGF-I synthesis, phosphorylation of STATS, expression of suppressors of cytokine signaling. Any cell type that is responsive to a polypeptide of the invention, or any tissue containing such responsive cells, can be used to assess biological activity, including cell lines and explants. Cell lines can be obtained from standard commercial sources and from depositories such as The American Type Culture Collection. The present polypeptides can also be evaluated in vivo.

The polypeptides of the invention can be chemically synthesized, obtained from natural sources (insofar as they constitute fragments of a naturally occurring GHBP), or purified from cells in which they are recombinantly produced. Of course, molecular techniques can be used to express polypeptides having a sequence that is identical to a portion of a GHBP or biologically active variants thereof; the methods required for polypeptide synthesis, expression and purification are well known in the art. For example, polypeptides can be chemically synthesized using standard f-moc chemistry and purified using high pressure liquid chromatography (HPLC). Fragments of a GHBP and biologically active variants thereof can be purified by any method known in the art, including without limitation, fractionation, centrifugation, and chromatography (e.g., gel filtration, ion exchange chromatography, reverse-phase HPLC and immunoaffinity purification).

The polypeptides may be, but are not necessarily, substantially pure. A polypeptide of the invention, whether it contains a sequence that is identical to a portion of a GHBP or a biologically active variant thereof, should be considered substantially pure when it has been separated from a substantial amount of the material with which it was previously associated (e.g., cellular components where the polypeptide is recombinantly produced or reagents where the polypeptide is chemically synthesized). For example, a polypeptide of the invention is substantially pure when it is present in a composition in which it constitutes at least or about 60% of the composition by weight (e.g., at least or about 65%, 70%, 80%, 90%, 95%, or 99%). If tested by electrophoresis, a substantially pure polypeptide will yield a single major band on a non-reducing polyacrylamide gel.

To produce a recombinant polypeptide of the invention, a nucleic acid sequence encoding the polypeptide can be incorporated into (e.g., ligated into) an expression vector and used to transform a prokaryotic cell (e.g., a bacterial cell) or transfect a eukaryotic host cell (e.g., an insect, yeast, or mammalian host cell). In general, nucleic acid constructs can include one or more regulatory sequences operably linked to a nucleic acid sequence encoding a polypeptide of the invention. Regulatory sequences (e.g., promoters, enhancers, polyadenylation signals, and terminators) do not typically encode a protein/polypeptide, but instead affect the expression of a nucleic acid sequence. Such transformed or transfected cells can then be used, for example, for large or small scale production of the selected fragment of a GHBP (or a biologically active variant thereof) by methods known in the art. In essence, such methods involve culturing the cells under conditions suitable for production of the polypeptide and isolating the polypeptide from the cells or from the culture medium.

A construct can include a tag sequence designed to facilitate subsequent manipulations of the expressed nucleic acid sequence. For example, the tag can facilitate purification or localization. Tag sequences, such as green fluorescent protein (GFP), glutathione S-transferase (GST), c-myc, hemagglutinin, p-galactosidase, or FLAG tag (Kodak) sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include, without limitation, pBAD (Invitrogen, Carlsbad, Calif.), the pTYB family of vectors (New England Biolabs), and pGEMEX vectors (Promega); representative mammalian expression vectors include, without limitation, pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include, without limitation, pBacPAK8 or pBacPAK9 (Clontech), and p2Bac (Invitrogen); and representative yeast expression vectors include, without limitation, MATCHMAKER (Clontech) and pPICZ A, B, and C (Invitrogen).

In bacterial systems, *Escherichia coli* can be used to express a fragment of a GHBP or a biologically active variant thereof. For example, the *E. coli* strain DH1OB (Invitrogen) can be transformed with the gram negative broad host range vector, pCM66 containing a nucleic acid sequence encoding a fragment of a GHBP protein. In another example, BL-21 cells can be transformed with a pGEX vector containing a nucleic acid sequence encoding a polypeptide of the invention. The transformed bacteria can be grown exponentially and then stimulated with isopropylthiogalactopyranoside (IPTG) prior to harvesting. In general, the polypeptides produced from a pGEX expression vector can be purified from lysed cells by adsorption to glutathione-agarose beads followed by elution in the presence of free glutathione. The pGEX vectors can be designed to include thrombin or factor Xa protease cleavage sites so that the expressed polypeptide can be released from the GST moiety.

The invention further encompasses peptidomimetics of fragments of a GHBP, which are small, protein-like polymers containing non-peptidic structural elements that are capable of mimicking or antagonizing the biological actions of a natural parent peptide (here, a fragment of a GHBP or a biologically active variant thereof). In addition to being synthetic, non-peptide compounds, peptidomimetics can have a three-dimensional conformation (i.e., a "peptide motif") that is substantially the same as the three-dimensional conformation of a selected polypeptide. The peptide motif provides the peptidomimetic compound with the ability to bind the receptor in a manner qualitatively identical to that of the parent peptide from which the peptidomimetic was derived. Peptidomimetic compounds can have additional characteristics that enhance their therapeutic utility, such as an increased biological half-life.

The peptidomimetics typically have a backbone that is partially or completely non-peptide, but with side groups that are identical to the side groups of the amino acid residues that occur in the peptide on which the peptidomimetic is based. Several types of chemical bonds (e.g., ester, thioester, thioamide, retroamide, reduced carbonyl, dimethylene and ketomethylene bonds) are known in the art to be generally useful substitutes for peptide bonds in the construction of protease-resistant peptidomimetics and can be used in the context of the present peptides).

Any peptidomimetic that has a sufficient amount of biological activity (e.g., an amount that renders the peptidomimetic experimentally or clinically useful) can be used.

As noted above in describing suitable expression vectors, the present polypeptides can include a tag, which may also be referred to as a reporter or marker (e.g., a detectable marker). A detectable marker can be any molecule that is covalently linked to the fragment of a GHBP or a biologically active fragment thereof that allows for qualitative and/or quantitative assessment of the expression or activity of the tagged peptide. The activity can include a biological activity, a physico-chemical activity, or a combination thereof. Both the form and position of the detectable marker can vary, as long as the labeled peptide retains biological activity. Many different markers can be used, and the choice of a particular marker will depend upon the desired application. Labeled polypeptides can be used, for example, for evaluating the phamacokinetics of the polypeptide both in cell-based systems and in whole animal models.

Suitable markers include, for example, enzymes, photoaffinity ligands, radioisotopes, and fluorescent or chemiluminescent compounds. Methods of introducing detectable markers into peptides are well known in the art. Markers can be added during synthesis or post-synthetically. Recombinant polypeptides can also be labeled by the addition of labeled precursors (e.g., radiolabeled amino acids) to the culture medium in which the transformed cells are grown. In some embodiments, analogues or variants of the polypeptides of the invention can be used in order to facilitate incorporation of detectable markers. For example, any N-terminal phenylalanine residue can be replaced with a closely related aromatic amino acid, such as tyrosine, that can be easily labeled with $^{125}$I. In some embodiments, additional functional groups that support effective labeling can be added to the polypeptides. For example, a 3-tributyltinbenzoyl group can be added to the N-terminus of the native structure; subsequent displacement of the tributyltin group with $^{125}$I will generate a radiolabeled iodobenzoyl group.

Nucleic Acids:

We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a naturally occurring GHBP or a biologically active variant thereof.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated and/or synthetic nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated and/or synthetic nucleic acid also refers to a DNA molecule that is incorporated into a vector, an autonomously replicating plasmid, a virus, or into the genomic DNA of a prokaryote or eukaryote. In addition, an isolated and/or synthetic nucleic acid can include an engineered nucleic acid such as a DNA molecule that is part of a hybrid or fusion nuThanks Myracleic acid.

Synthetic nucleic acid molecules can be produced by standard techniques. For example, polymerase chain reaction (PCR) techniques can be used to obtain a synthetic nucleic acid containing a nucleotide sequence described herein, including nucleotide sequences encoding a polypeptide described herein (i.e. a fragment of a GHBP protein or a biologically active variant thereof). PCR can be used to amplify specific sequences from DNA as well as RNA, including sequences from total genomic DNA or total cellular RNA. Various PCR methods are described in, for example, PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid (as one may wish to do, for example, when making a biologically active variant of a fragment of a GHBP protein).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of a GHBP-encoding DNA (in accordance with, for example, the formula above).

Two nucleic acids or the polypeptides they encode may be described as having a certain degree of identity to one another. For example, a fragment of a GHBP protein and a biologically active variant thereof may be described as exhibiting a certain degree of identity. Alignments may be assembled by locating short GHBP sequences in the Protein Information Research (PIR) site (http://pir.georgetown.edu), followed by analysis with the "short nearly identical sequences" Basic Local Alignment Search Tool (BLAST) algorithm on the NCBI website (http://www.ncbi.nlm.nih.gov/blast).

As used herein, the term "percent sequence identity" refers to the degree of identity between any given query sequence and a subject sequence. For example, a naturally occurring GHBP can be the query sequence and a fragment of a GHBP protein can be the subject sequence. Similarly, a fragment of a GHBP protein can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., Nucleic Acids Res. 31:3497-3500, 2003.

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pair wise alignment of nucleic acid sequences, the following default parameters are used: word size: 2; window size: 4; scoring method: percentage; number of top diagonals: 4; and gap penalty: 5. For multiple alignments of nucleic acid sequences, the following parameters are used: gap opening penalty: 10.0; gap extension penalty: 5.0; and weight transitions: yes. For fast pair wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express fragments of a GHBP protein. A recombinant nucleic acid construct comprises a nucleic acid encoding a fragment of a GHBP as described herein, operably linked to a regulatory region suitable for expressing the fragment of a GHBP protein in the cell. Thus, a nucleic acid can comprise a coding sequence that encodes any of the fragments of a GHBP protein as set forth in, for example, in SEQ ID NO:11 or another polypeptide as described herein (e.g., a polypeptide shown in Table 1 or represented by, for example, SEQ ID NOs:1-10, SEQ ID NO:14 or to a homolog or ortholog thereof). In some cases, a recombinant nucleic acid construct can include a nucleic acid comprising a coding sequence, a gene, or a fragment of a coding sequence or gene in an antisense orientation so that the antisense strand of RNA is transcribed. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for a given fragment of a GHBP can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG tag (Kodak, New Haven, Conn.) sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

In some embodiments, the compositions can include GH or a biologically active fragment thereof. GH is a 22 kilodalton, 191 amino acid neuropeptide belonging to a family or proteins that includes prolactins, lactogens and proliferins. It is synthesized in the somatotrophs of the anterior pituitary gland. GH is responsible for a host of biological effects such as linear growth, lactation, activation of macrophages, cell differentiation, electrolyte balance and insulin-like and diabetogenic effects. Four isoforms, resulting from alternative splicing events, have been identified. Growth hormone is also highly conserved evolutionarily.

The NCBI reference sequence for hGH isoform 1 precursor can be found at Genbank under accession number NP 000506.2, public GI:13027812. The NCBI reference sequence for isoform 2 precursor can be found at Genbank under accession number NP 072053.1, public GI:13027814. The NCBI reference sequence for isoform 3 precursor can be found at Genbank under accession number NP_072054.1, public GI:13027816. The NCBI reference sequence for isoform 4 precursor can be found at Genbank under accession number NP 072055.1, public GI:13027818. The NCBI reference sequence for isoform 5 precursor can be found at Genbank under accession number NP 072056.1, public GI:13027820.

The fragments of GHBP of the invention can be combined with GH. The relative amounts of the fragments of GHBP and GH can vary, but the combinations can include, for example, GH: hGHBP fragments in a 1:1 or 2:1 ratio.

hGH may isolated from in its natural form from the pituitary gland of human cadavers, or may be produced recombinantly known genetic engineering techniques. Recombinant production of hGH can yield a variety of hGH species, including a 191 amino acid native species (commonly known as Somatropin), as described for example in U.S. Pat. Nos. 4,670,393, 5,424,199, 5,633,352 and 5,795,745 (the disclosures of which are hereby incorporated by reference) or a 192 amino acid species, met-hGH, having N-terminal methionine (met) (commonly known as Somatrem), such as that described in U.S. Pat. No. 4,658,021, which is hereby incorporated by reference.

Commercially available recombinant hGH is marketed under the trade names GENOTROPIN (Pfizer), HUMATROPE (Lilly), NORDITROPIN (Novo), NUTRIPIN (Genentech), SAIZEN (Merck Serono), SEROSTIM (EMD Serono) and OMNITROPE (Sandoz). Recombinant hGH for bovine use is marketed under the trade name POSILAC (Lilly).

Administration and Formulation

The compositions described herein can be administered directly to a mammal, which we may also refer to as a "subject" or "patient." Generally, the compositions, e.g., fragments of an HGBP, can be suspended in a pharmaceutically acceptable carrier (e.g., physiological saline or a buffered saline solution) to facilitate their delivery (e.g., by intravenous administration).

As described above, the fragments of an HGBP of the present invention can be prepared in a variety of ways known to one of ordinary skill in the art. Regardless of their original source or the manner in which they are obtained, the compositions of the invention can be formulated in accordance with their use. For example, the fragments of an HGBP can be formulated within compositions for application to cells in tissue culture or for administration to a patient. When employed as pharmaceuticals, any of the present fragments of an HGBP can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, one or more of the fragments of HGBP described herein in combination with one or more pharmaceutically acceptable carriers. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active fragments of HGBP, soft and hard gelatin capsules, suppositories, sterile injectable solutions, and sterile packaged powders. As is known in the art, the type of diluent can vary depending upon the intended route of administration. The resulting compositions can include additional agents, such as preservatives. The fragments of HGBPs may also be applied to a surface of a device (e.g., a catheter) or contained within a pump, patch, or other drug delivery device. The fragments of HGBP of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary). In preparing a formulation, the active ingredients can be milled to provide the appropriate particle size prior to combining with the other ingredients. If the active ingredient is substantially water insoluble, it can be milled to a particle size of less than 200 mesh. If the active ingredient is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of an ingredient of the present invention. When referring to these preformulation compositions as homogeneous, the active ingredient is typically dispersed evenly throughout the composition so the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/or known in the art. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner. The compositions administered to a patient can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the preparations typically will be between about 3 and 11, for example, between about 5 to 9, between 6 and 7, between 7 and 8. It will be understood that use of certain of the foregoing excipients, carriers, or stabilizers could result in the formation of pharmaceutical salts.

The proportion or concentration of the fragments of HGBPs of the invention in a pharmaceutical composition can vary depending upon a number of factors including dosage, chemical characteristics (e.g., hydrophobicity), and the route of administration. For example, the fragments of HGBPs of the invention can be provided in an aqueous physiological buffer solution containing about 0.1 to about 10% w/v of the fragments of HGBP for parenteral administration.

The present formulations can encompass mixtures of the polypeptides of the invention, and the formulations can include a combination of peptides of 2, 3, 4, 5, 6, 7, 8, 9, 10, 15, 20, 30, or more different amino acid sequences. For example, the formulation can include a combination of any of SEQ ID NOs.:1-10. The formulation can also include a mixture of polypeptides based on post-synthetic modifications or other post-translational modifications. Where nucleic acids are formulated as pharmaceutical compositions, the nucleic acids can similarly encode polypeptides in the configurations just described.

In some embodiments, the fragments of GHBP can be formulated as part of a complex. For example, the fragments can be joined, either covalently or non-covalently to a larger carrier protein, for example, albumin. The fragments of GHBP and the carrier protein can also be synthesized as separate entities (by either chemical synthetic or recombinant methods) and then linked together by standard chemical methods known in the art. Chemical cross-linking agents can be homo-bifunctional (the same chemical reaction takes place at each end of the linker) or hetero-bifunctional (different chemical reactions take place at the ends of the linker). The chemistries available for such linking reactions include, but are not limited to, reactivity with sulfhydryl, amino, carboxyl, diol, aldehyde, ketone, or other reactive groups using electrophilic or nucleophilic chemistries, as well as photochemical cross-linkers using alkyl or aromatic azido or carbonyl radicals. In some embodiments, the fragments of GHBP and the carrier can be a fusion protein generated by recombinant DNA techniques.

Alternatively or in addition, the fragments of GHBP and the carrier can be connected through a linking polymer. Examples of linking molecules include, but are not limited to linear or branched polymers or co-polymers (e.g., polyalkylene, poly(ethylene-lysine), polymethacrylate, polyamino acids, poly- or oligosaccharides, dendrimers). The fragments of GHBP and the carrier can be attached to the linking molecule or microparticle through a non-covalent high affinity linkage, e.g., streptavidin-biotin high affinity binding or chemical cross-linking techniques as described above. In another embodiment, the fragments of GHBP can be complexed, with or without a carrier protein, in a microparticle or nanoparticle, for example, micelles, liposomes, fullerenes, nanotubes, or other colloidal complexes such as lipoproteins.

The therapeutic dosage of the compositions of the present invention can vary according to, for example, the particular use for which the treatment is made, the manner of administration of the compositions, the health and condition of the patient, and the judgment of the attending clinician. The proportion or concentration of a fragments of GHBP of the invention in a pharmaceutical composition can vary depending upon a number of factors including dosage, chemical characteristics (e.g., hydrophobicity), and the route of administration. For example, the compositions of the invention can be provided in an aqueous physiological buffer solution containing about 0.1 to about 10% w/v of the fragments of HGBP for parenteral administration. Some typical dose ranges are from about 1 ug/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compositions selected, formulation of the excipient, and its route of administration. Effective doses can be extrapolated from dose-response curves derived from in vitro or animal model test systems.

Any composition described herein can be administered to any part of the host's body for subsequent delivery to a target cell. A composition can be delivered to, without limitation, blood, lungs, intestines, muscle tissues, skin, the peritoneal cavity the cerebrospinal fluid, joints, nasal mucosa, or the brain of a mammal. In terms of routes of delivery, a composition can be administered by subcutaneous, intramuscular intravenous, intracranial, intraperitoneal, intramuscular, intrarectal, intravaginal, intrathecal, intratracheal, intradermal, or transdermal injection, by oral or nasal administration, or by gradual perfusion over time. In a further example, an aerosol preparation of a composition can be given to a subject by inhalation.

The dosage required will depend on the route of administration, the nature of the formulation, the nature of the patient's illness, the patient's size, weight, surface area, age, and sex, other drugs being administered, and the judgment of the attending clinicians. Suitable dosages are in the range of 0.01-1,000 mg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compositions in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a composition can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present composition can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant side effects in the patient. Such an amount can be determined by assessing a patient's response after administration of a known amount of a particular composition. In addition, the level of side effects, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant side effects can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

Methods of Treatment

The compositions disclosed herein are generally and variously useful for treatment of growth disorders, cachexia, and other conditions in which the affected cells or tissues are responsive to GH. Growth disorders encompass a wide range of conditions and can result from genetic mutations, acquired disease or environmental deficiencies. Exemplary growth disorders related to GH deficiency include GH-deficiency in children and GH-deficiency in adults. Other growth disorders amenable to treatment with the compositions of the invention include those growth disorders unrelated to GH deficiency, e.g, Turner Syndrome, Praeder-Willi Syndrome, chronic kidney disease, small bowel syndrome, SHOX deletion, Noonan Syndrome, small for gestational age, and idiopathic short stature. The compositions of the invention are also useful for the treatment of muscle-related disorders, e.g, cachexia due to AIDS. In some embodiments, the compositions may be useful for cardiovascular disease, neurological injuries, cerebral palsy and wound healing.

A subject is effectively treated whenever a clinically beneficial result ensues. This may mean, for example, a complete resolution of the symptoms associated with a growth disorder, a decrease in the severity of the symptoms associated with a growth disorder, or a slowing of the progression of symptoms associated with a growth disorder. For many subjects, particularly children, a response is measured in terms of increased height and an increased rate of growth. In adults, a response can be noted in terms of decreased fat mass, alterations in total blood cholesterol, LDL-C and triglycerides, increased bone density, and increased energy levels. In some subjects, for example, Praeder-WIlli patients, a response may be noted in terms of increased muscle mass, and improvement in hypotonia. In subjects having AIDS-related cachexia, a response may be noted in terms of increased muscle mass in increased energy levels.

These methods can further include the steps of a) identifying a subject (e.g., a patient and, more specifically, a human patient) who has a growth disorder; and b) providing to the subject a composition described herein. An amount of such a composition provided to the subject that results in a complete resolution of the symptoms associated with a growth disorder, a decrease in the severity of the symptoms associated with a growth disorder, or a slowing of the progression of symptoms associated with a growth disorder is considered a therapeutically effective amount. The present methods may also include a monitoring step to help optimize dosing and scheduling as well as predict outcome.

The methods disclosed herein can be applied to a wide range of species, e.g., humans, non-human primates (e.g., monkeys), horses, pigs, cows or other livestock, dogs, cats or other mammals kept as pets, rats, mice, or other laboratory animals. The compositions described herein are useful in therapeutic compositions and regimens or for the manufacture of a medicament for use in treatment of conditions as described herein (e.g., a growth disorder.) In agriculturally important animals, e.g., dairy cows, the compositions may be administered to stimulate milk production.

Effective doses can be extrapolated from dose-response curves derived from in vitro or animal model test systems. Any method known to those in the art can be used to determine if a particular response is induced. Clinical methods that can assess the degree of a particular disease state can be used to determine if a response is induced. For example, physical parameters such as a subject's height, weight, muscle mass and bone density can be measured. Alternatively or in addition, serum markers, imaging techniques, e.g., ultrasound and x-rays.

The compositions may also be administered in conjunction with other therapeutic modalities. These therapeutic modalities will vary according to the particular disorder, but can include, for example, dietary remedies and treatment with other hormones, e.g., GH, sex steroid hormones, cortisol or thyroid hormones.

Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Articles of Manufacture

The compositions described herein can be packaged in suitable containers labeled, for example, for use as a therapy to a growth disorder. The containers can include the fragments of HGBP of the invention and one or more of a suitable stabilizer, carrier molecule, flavoring, and/or the like, as appropriate for the intended use. In some embodiments, that kits can include GH. Accordingly, packaged products (e.g., sterile containers containing one or more of the compositions described herein and packaged for storage, shipment, or sale at concentrated or ready-to-use concentrations) and kits, including at least one composition of the invention and instructions for use, are also within the scope of the invention. A product can include a container (e.g., a vial, jar, bottle, bag, or the like) containing one or more compositions of the invention. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the composition therein should be administered (e.g., the frequency and route of administration), indications therefor, and other uses. The compositions can be ready for administration (e.g., present in dose-appropriate units), and may include a pharmaceutically acceptable adjuvant, carrier or other diluent and/or an additional therapeutic agent. Alternatively, the compositions can be provided in a concentrated form with a diluent and instructions for dilution.

In one aspect, the present disclosure provides a recombinant polypeptide comprising a fragment of a growth hormone binding protein (GHBP),where in the polypeptide comprises an amino acid sequence selected from the group consisting of: Ser-Pro-Glu-Arg-Glu-Thr-Phe-Ser (SEQ ID NO:1); Arg-Arg-Asn-Thr-Gln-Glu-Trp-Thr-Gln-Glu-Trp-Lys-Glu (SEQ ID NO:2); Arg-Arg-Asn-Thr-Gln-Glu (SEQ ID NO:3); Trp-Thr-Gln-Glu-Trp-Lys-Glu (SEQ ID NO:4); Thr-Ser-Ile-Trp-Ile-Pro (SEQ ID NO:5); Val-Asp-Glu-Ile-Val-Gln-Pro-Asp (SEQ ID NO:6); Thr-Ser-Ile-Trp-Ile-Pro-Tyr-Cys-Ile-Gly-Lys-Cys-Phe-Ser-Val-Asp-Glu-Ile-Val-Gln-Pro-Asp (SEQ ID NO:7); Thr-Ser-Ile-Trp-Ile-Pro-Tyr-Gly-Ser-Val-Asp-Glu-Ile-Val-Gln-Pro-Asp (SEQ ID NO:8); Lys-Val-Asp-Lys-Glu-Tyr-Glu SEQ ID NO:9); and Arg-Val-Arg-Ser-Lys-Gln-Arg (SEQ ID NO:10).

In certain embodiments, the present disclosure provides a recombinant polypeptide comprising a fragment of a growth hormone binding protein (GHBP),where in the polypeptide comprises an amino acid sequence that is at least 90% identical to an amino acid sequence selected from the group consisting of SEQ ID NO:1-10.

In one aspect, the present disclosure provides a pharmaceutical composition comprising a therapeutically effective amount of any one of the polypeptides of claim 1. In one embodiment, the pharmaceutical composition comprises a pharmaceutically acceptable carrier. In one embodiment, the pharmaceutical composition comprises a liposome, a nanoparticle or a carrier protein.

In one embodiment, the pharmaceutical composition further comprising a growth hormone polypeptide or fragment thereof. In one embodiment, the growth hormone polypeptide is recombinant. In one embodiment, the growth hormone polypeptide is human growth hormone.

In one aspect, the present disclosure provides a synthetic nucleic acid sequence encoding any one of the polypeptides of claim 1, as well as expression vectors, host cells, and kits containing the same.

In one aspect, the present disclosure provides a kit comprising (a) the polypeptide or the pharmaceutical composition described herein and optionally, a growth hormone polypeptide; and (b) instructions for use thereof.

In one aspect, the present disclosure provides a method of treating a subject who is at risk for or has a growth disorder, the method comprising administering a therapeutically effective amount of the composition described herein. In one embodiment, the method further comprising identifying a subject in need of treatment. In one embodiment, the composition is administered until a symptom of the growth disorder improves. In one embodiment, the growth disorder is growth hormone deficiency, Turner Syndrome, Praeder-Willi Syndrome, short-stature homeobox gene (SHOX) deficiency, idiopathic short stature; or chronic renal failure. In one embodiment, the subject is human. In one embodiment, the subject is under 21 years of age.

In one aspect, the present disclosure also provides a method of treating a subject who is at risk for or has cachexia, the method comprising administering a therapeutically effective amount of the composition disclosed herein. In one embodiment, the cachexia is acquired immunodeficiency syndrome-related cachexia. In one embodiment, the method further comprising identifying a subject in need of treatment. In one embodiment, the composition in said method is administered until a symptom of cachexia improves.

EXAMPLES

Example 1: Materials and Methods

Peptides:

Peptides were custom synthesized by aapptec (advanced 95 automated peptide protein technologies, Louisville Ky., 40228-1027, USA). Peptide sequences and the corresponding amino acid segment in hGHBP are shown in Table 1.

TABLE 1

Peptide Sequences

| Peptide # | Length (# of AA) | Sequence | Corresponding fragment in hGHBP |
|---|---|---|---|
| 1 | 8 | S-P-E-R-E-T-F-S (SEQ ID NO.: 1) | Serine-40 to Serine-47 |
| 2 | 13 | R-R-N-T-Q-E-W-T-Q-E-W-K-E (SEQ ID NO.: 2) | Arginine-70 to Glutamate-82 |
| 3 | 6 | R-R-N-T-Q-E (SEQ ID NO.: 3) | Arginine-70 to Glutamate-76 |
| 4 | 7 | W-T-Q-E-W-K-E (SEQ ID NO.: 4) | Tryptophan-77 to Glutamate-82 |
| 5 | 6 | T-S-I-W-I-P (SEQ ID NO.: 5) | Threonine-101 to Proline-106 |
| 6 | 8 | V-D-E-I-V-Q-P-D (SEQ ID NO.: 6) | Valine-125 to Aspartate-132 |
| 7 | Variable | T-S-I-W-I-P-Y-C-I-G-K-C-F-S-V-D-E-I-V-Q-P-D* (SEQ ID NO.: 7) | Peptide 5 & Peptide 6 bridged without the Cysteine Double bond |
| 8 | Variable | T-S-I-W-I-P-Y-G-S-V-D-E-I-V-Q-P-D (SEQ ID NO.: 8) | Peptide 5 & Peptide 6 bridged using the Cysteine Double bond |
| 9 | 7 | K-V-D-K-E-Y-E (SEQ ID NO.: 9) | Lysine-203 to Glutamate-209 |
| 10 | 7 | R-V-R-S-K-Q-R (SEQ ID NO.: 10) | Arginine-211 to Arginine-217 |

*Peptide #7 has a cysteine-cysteine double bond.

Figure 2:
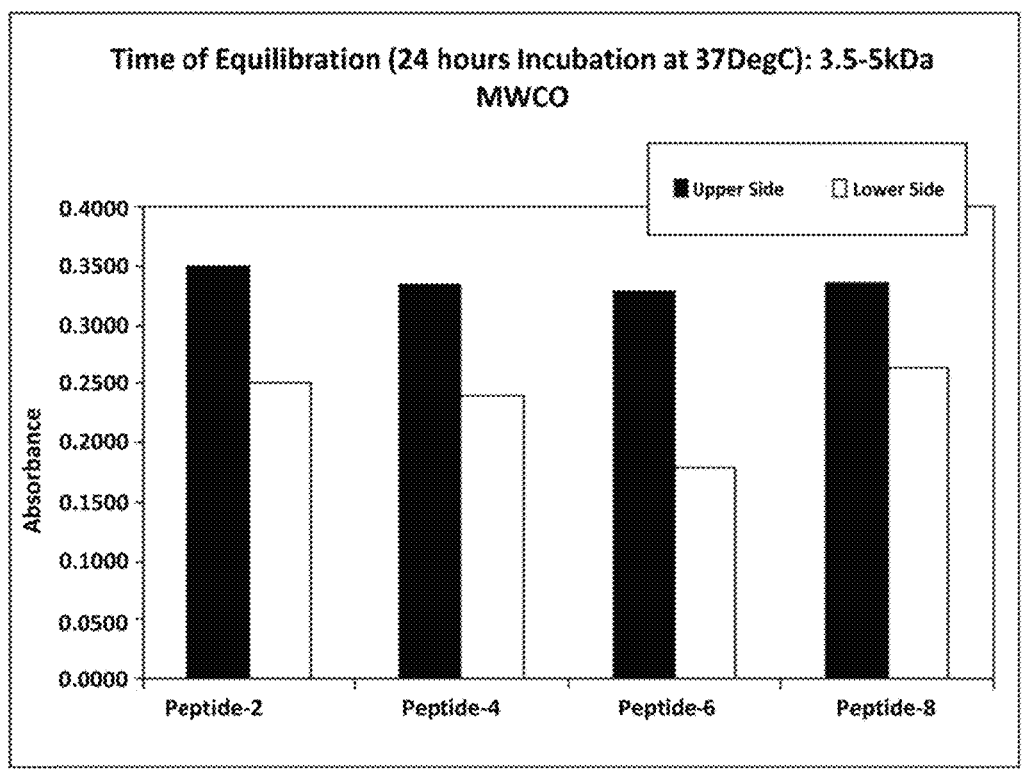
FIG. 2 is a graph depicting the results of an analysis of the effect of a 3.5-5 kDA MWCO membrane on diffusion of HGBP peptides of SEQ ID NO.:2, SEQ ID NO.:4, SEQ ID NO.:6, and SEQ ID NO.:8.

Equilibrium Dialysis: High Throughput Equilibrium Dialysis was performed using the 96-well Micro-Equilibrium Dialysis Device HTD (HTDialysis, LLC, CT, USA) according to the supplier's directions. The dialysis membrane was a SPECTRA/POR cellulose ester membrane. We tested a 3.5-5 kDa Molecular Weight Cut-off (MWCO) SPECTRA/POR membrane and a 12-14 kDa Molecular Weight Cut-off (MWCO) SPECTRA/POR membrane for their ability to allow peptide equilibration. Peptides were added to the upper chamber of each well of both a 3.5-5 kDa MWCO and a 12-14 kDa MWCO membrane and incubated at 37° C. with shaking at 200 rpm for 24 hours. Concentration of the peptide in the upper and lower chamber was assayed using MICRO-BCA Assay (Pierce) according to the supplier's directions. As shown in FIG. 1, peptide concentrations in the upper and lower chambers for the 12-14 kDa MWCO membrane were very similar. In contrast, as shown in FIG. 2, peptide concentrations in the upper and lower chambers for the 3.5-5 kDa MWCO membrane differed. These data suggested that peptide diffusion was more efficient with the 12-14 kDa MWCO membrane.

Figure 3:
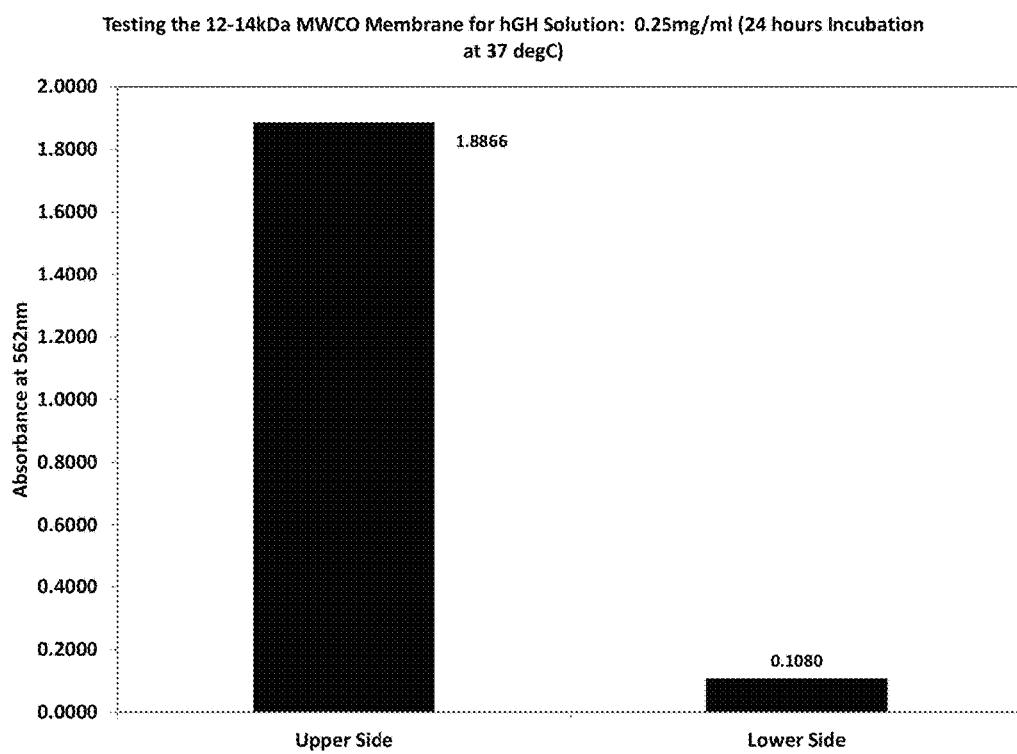
FIG. 3 is a graph depicting the results of an analysis of the effect of a 12-114 kDA MWCO membrane on diffusion of rhGH.

We then confirmed the ability of the 12-14 kDa MWCO membrane to retain the hGH. Lyophilized recombinant hGH (Bresagen, Adelaide, Australia) was dissolved in phosphate-buffered saline (PBS) plus 0.05% sodium azide. One-hundred uL of a 25 mg/mL solution plus 100 uL of PBS were added to the upper chamber of the micro-dialysis device fitted with a 12-14 kDa MWCO membrane and incubated at 37° C. with shaking at 200 rpm for 24 hours. Concentration of hGH in the upper and lower chamber was assayed using MICRO-BCA Assay (Pierce) according to the supplier's directions. As shown in FIG. 3, the majority of the hGH was retained by the 12-14 kDa MWCO membrane. We used the 12-14 kDa MWCO membrane for our binding assays.

Example 2: Analysis of hGH Binding to Peptides at a 1:1 Ratio

Figure 4A:
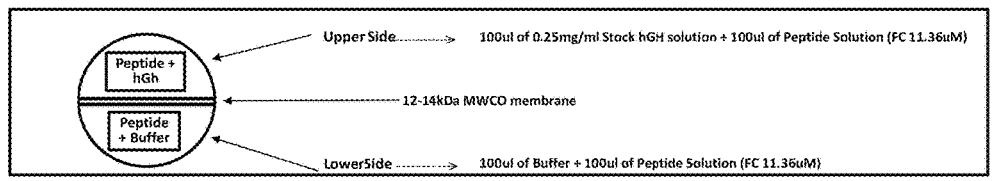
FIG. 4A is a cartoon depicting the configuration of an equilibrium dialysis experiment using a 1:1 ratio of rhGH:GHBP peptides.
Figure 5:
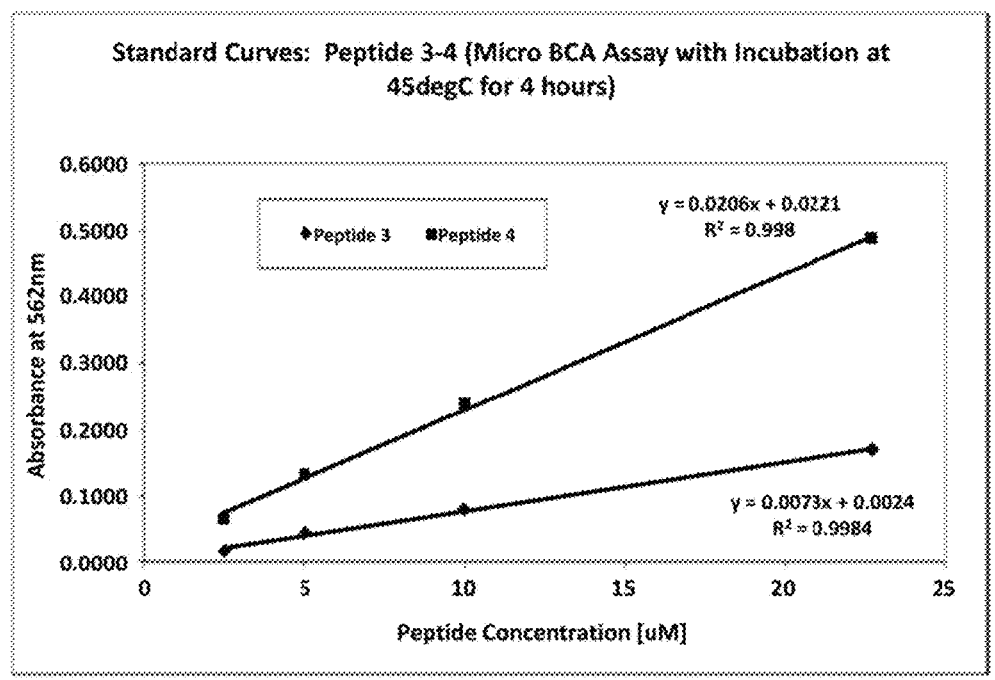
FIG. 5 is a graph depicting standard curves for peptides of SEQ ID NO.:3 and SEQ ID NO.:4.
Figure 6:
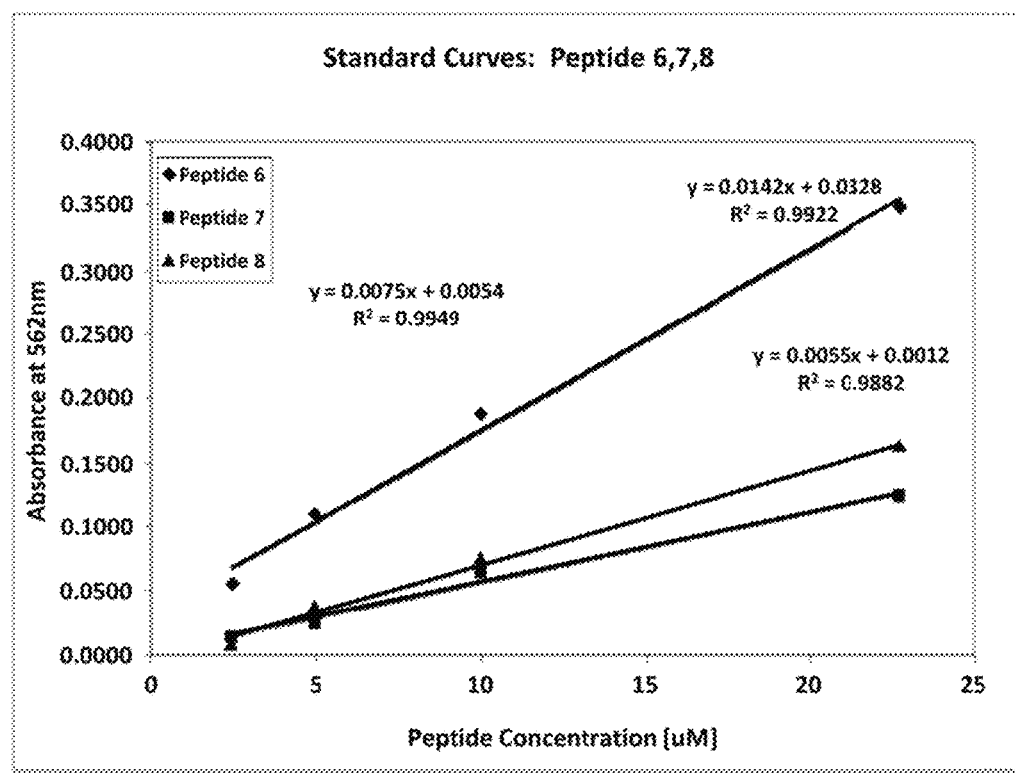
FIG. 6 is a graph depicting standard curves for peptides of SEQ ID NO.:6, SEQ ID NO.:7, and SEQ ID NO.:8.
Figure 7:
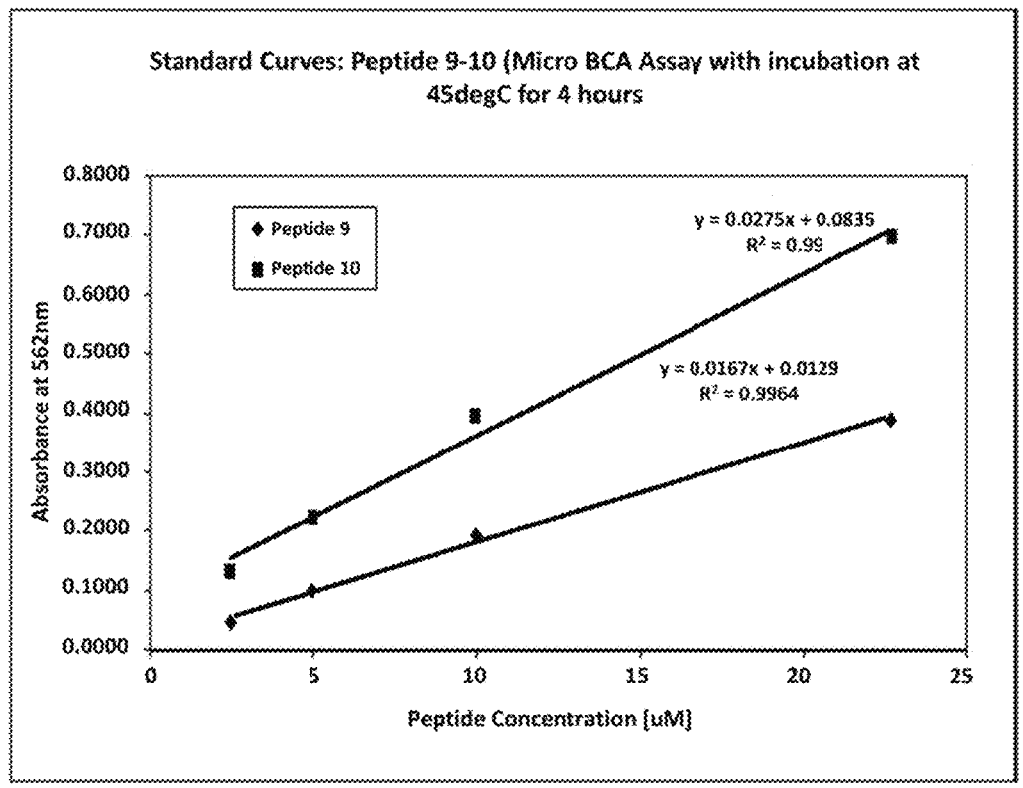
FIG. 7 is a graph depicting standard curves for peptides of SEQ ID NO.:9 and SEQ ID NO.:10.
Figure 14:
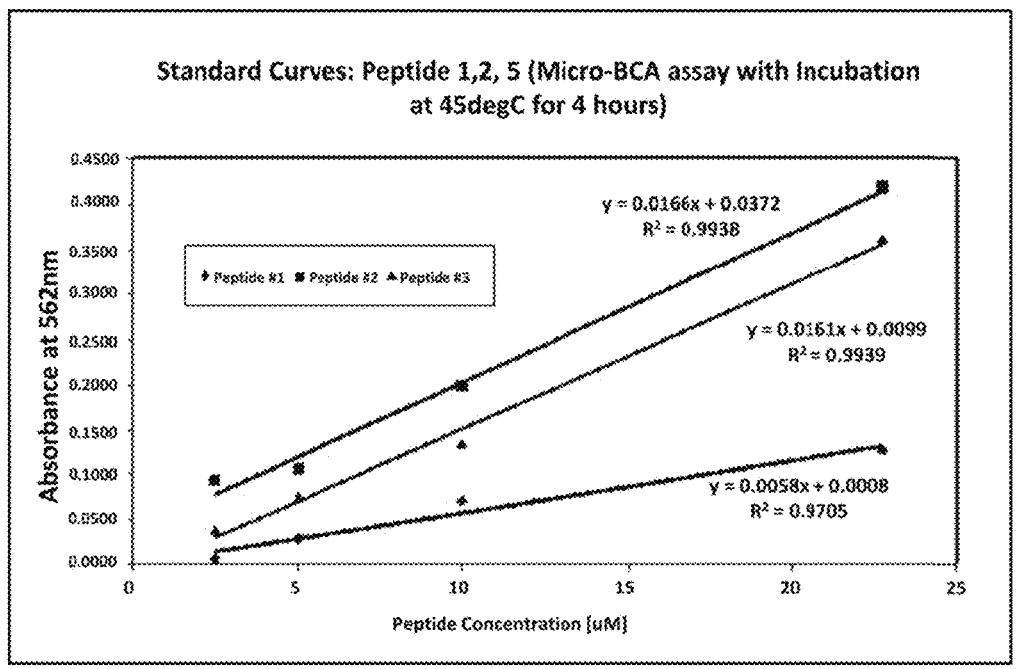
FIG. 14 is a graph depicting standard curves for peptides 1, 2 and 5.

This experiment was configured as shown in FIG. 4A. The upper chamber of each well received 100 uL of 0.25 mg/ml hGH and 100 uL of a 22.72 uM peptide solution. The lower chamber of each well received 100 uL of buffer and 100 uL of a 22.72 uM peptide solution. Thus, the starting concentration of peptide in both the upper and lower portion of each well was 11.36 uM. Plates were incubated at 37° C., with shaking at 200 rpm for 24 hours. Concentration of the peptide in the lower chamber was assayed using MICRO-BCA Assay (Pierce) essentially according to the supplier's directions. The assay was configured with a 1:2 sample: working reagent ratio and incubated 45° C. for 4 hours and read in a spectrophotometer at 562 nm. Concentrations of peptide in the lower chamber were determined based on the equations generated by the standard curves for each peptide. Standard curves for peptides 1, 2 and 5 are shown in FIG. 14. Standard curves for peptides 3 and 4 are shown in FIG. 5. Standard curves for peptides 6, 7, and 8 are shown in FIG. 6. Standard curves for peptides 9 and 10 are shown in FIG. 7.

Figure 4B:
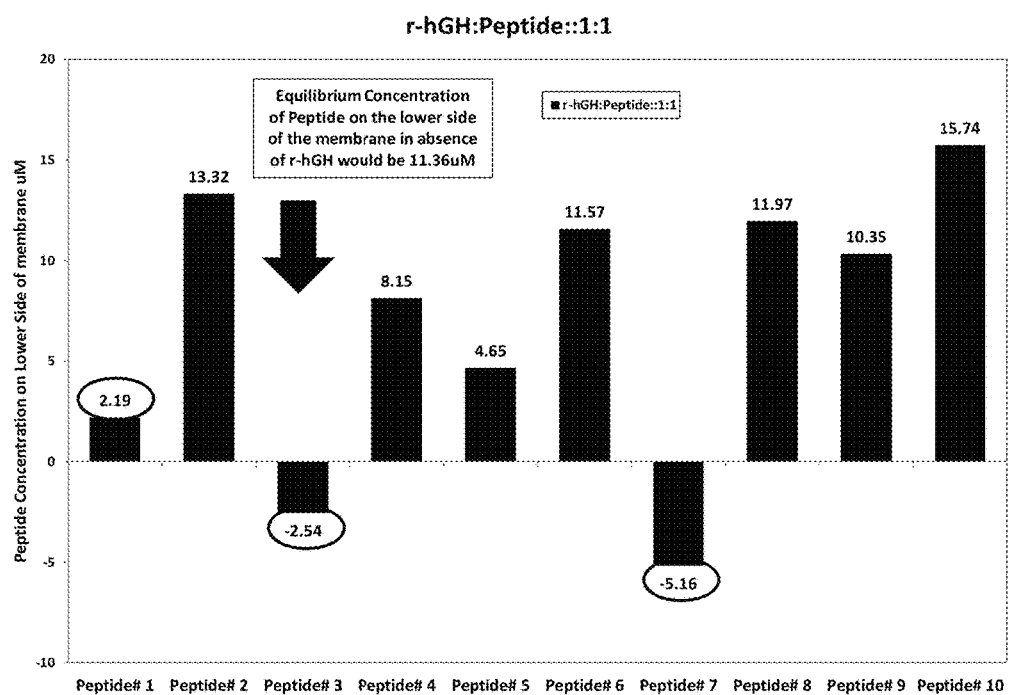
FIG. 4B is a graph depicting the results of an equilibrium dialysis experiment using a 1:1 ratio of rhGH:GHBP peptides.

The results of this experiment are shown in FIG. 4B. In the absence of rhGH, the concentration of each peptide in the lower chamber would have been 11.36 uM. As indicated, the concentrations of peptides 1, 3, and 7 in the lower chamber were substantially reduced in the presence of rhGH. These data suggested that, at a 1:1 ratio of rhGH:peptide, peptides 1, 3, and 7 bound rhGH.

Example 3: Analysis of hGH Binding to Peptides at a 2:1 Ratio

Figure 8A:
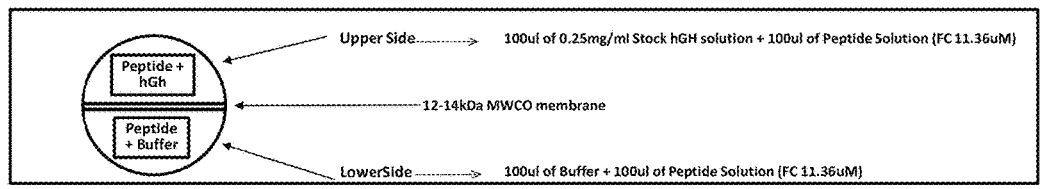
FIG. 8A is a cartoon depicting the configuration of an equilibrium dialysis experiment using a 2:1 ratio of rhGH:GHBP peptides.
Figure 8B:
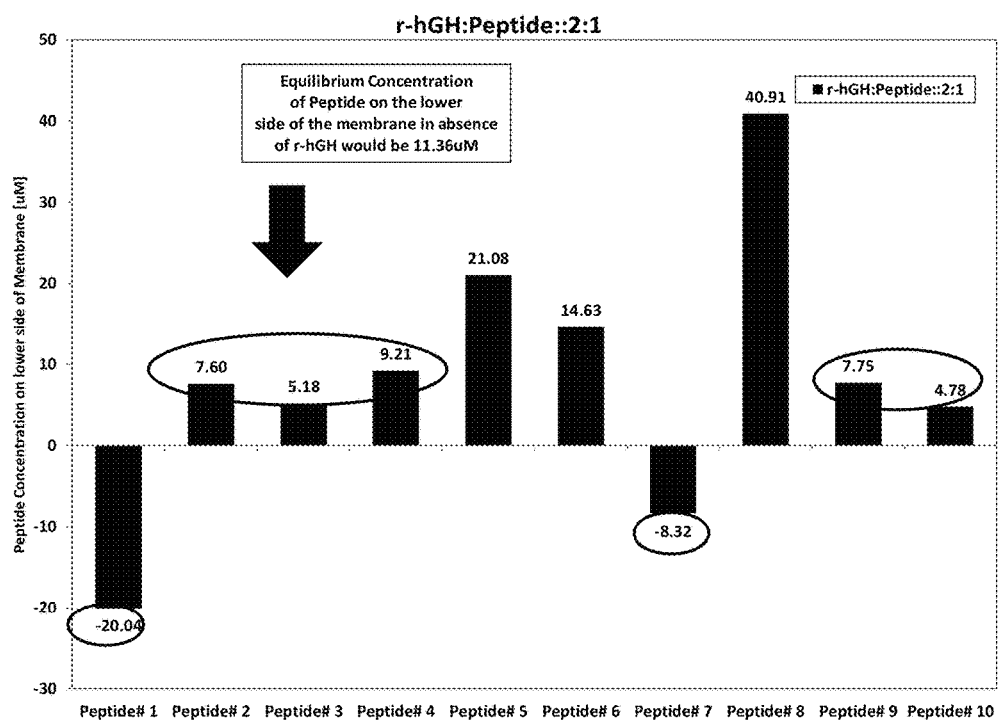
FIG. 8B is a graph depicting the results of an equilibrium dialysis experiment using a 2:1 ratio of rhGH:GHBP peptides.

This experiment was sent up as shown in FIG. 8A and carried out as described in Example 3 except that the rhGH stock solution was 0.5 mg/ml. The results of this experiment are shown in FIG. 8B. In the absence of rhGH, the concentration of each peptide in the lower chamber would have been 11.36 uM. As indicated, the concentrations of peptides 1-4, 7, 9, and 10 in the lower chamber were substantially reduced in the presence of rhGH. These data suggested that at a 2:1 ratio of rhGH:peptide, peptides 1-4, 7, 9, and 10 bound rhGH.

Example 4: Analysis of hGH Binding to Peptides at a 1:2 Ratio

Figure 9:
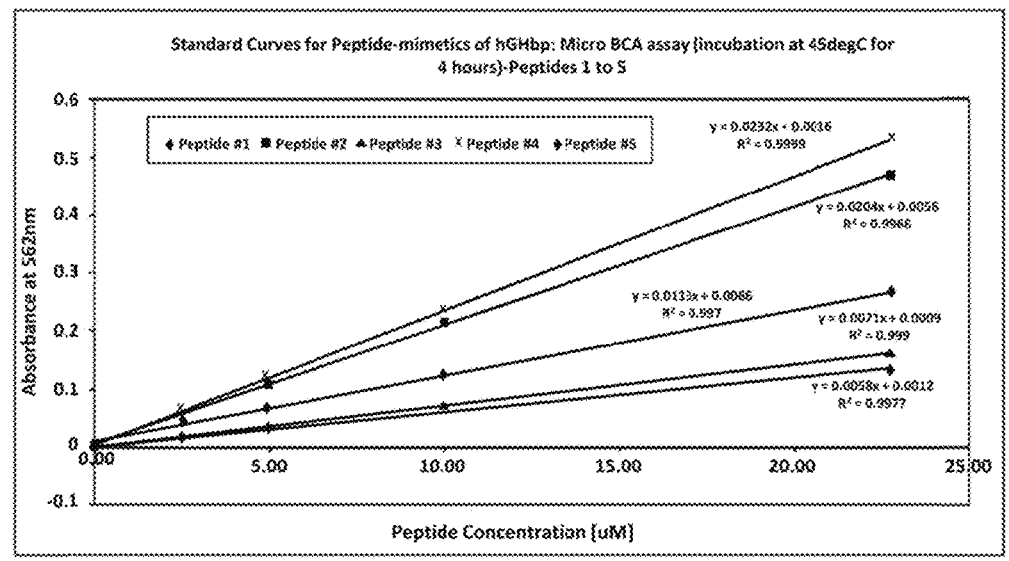
FIG. 9 is a graph depicting standard curves for peptides of SEQ ID NO.:1, SEQ ID NO.:2, SEQ ID NO.:3, SEQ ID NO.:4, and SEQ ID NO.:5.
Figure 10:
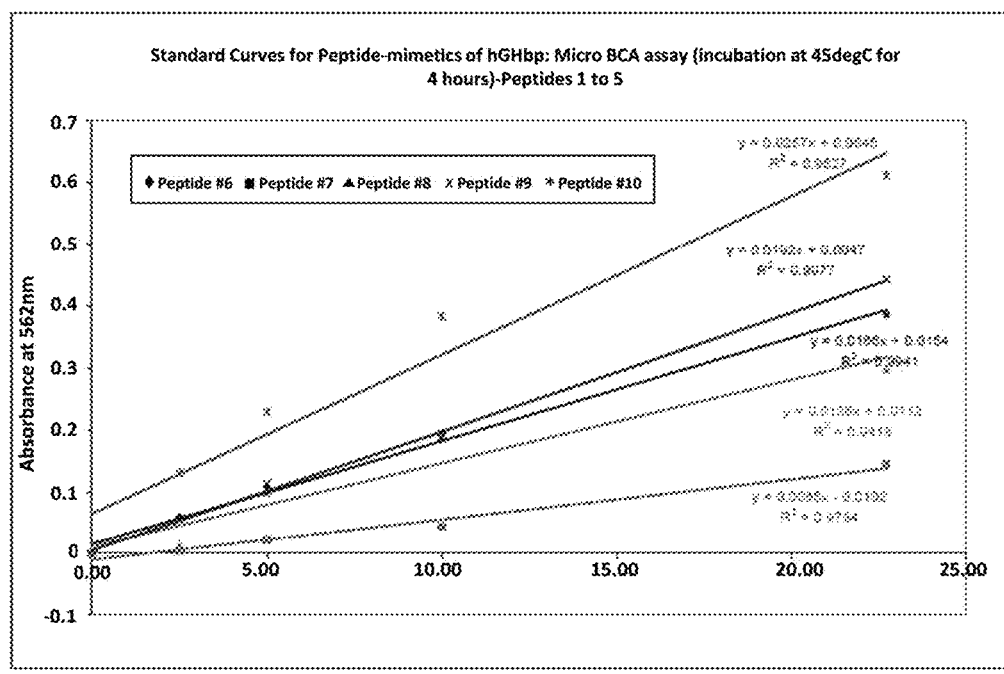
FIG. 10 is a graph depicting standard curves for peptides of SEQ ID NO.:6, SEQ ID NO.:7, SEQ ID NO.:8, SEQ ID NO.:9, and SEQ ID NO.:10.
Figure 11:
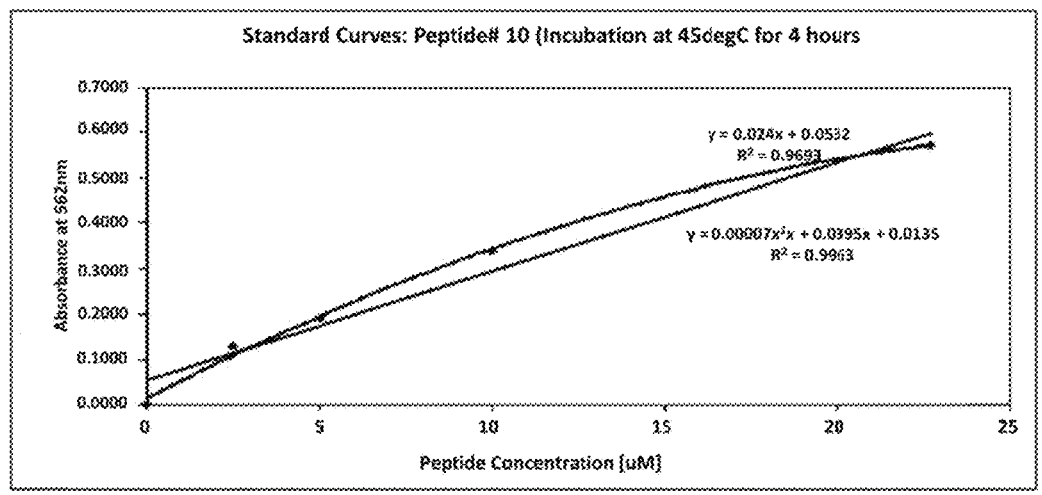
FIG. 11 is a graph depicting standard curves for peptide of SEQ ID NO.:10.
Figure 12:
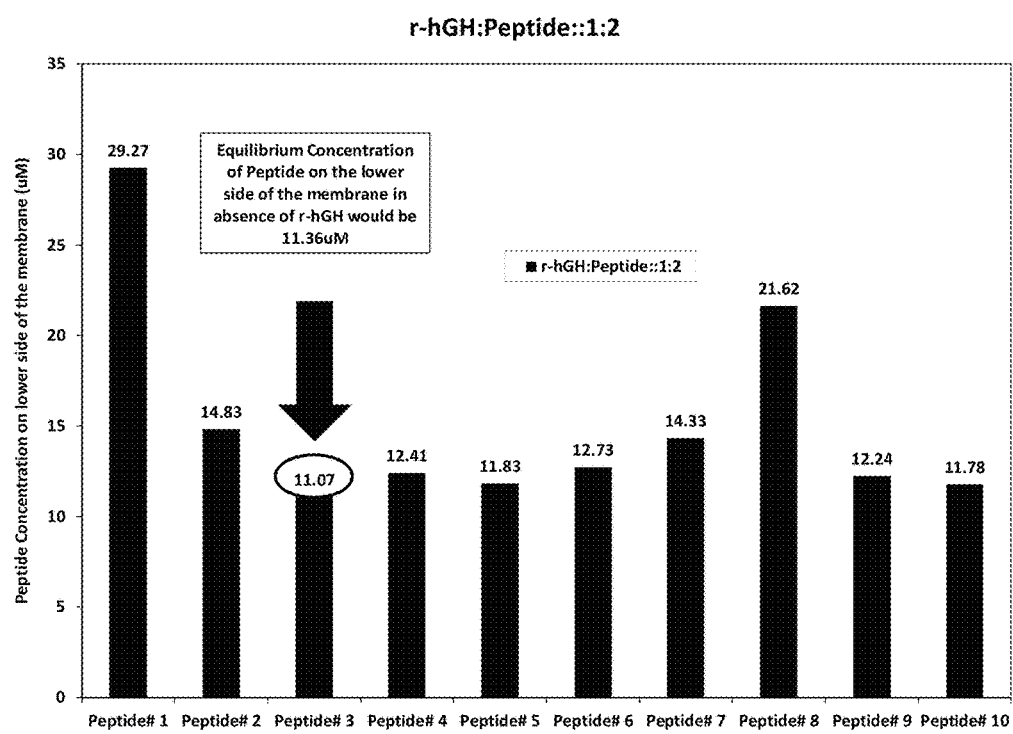
FIG. 12 is a graph depicting the results of an equilibrium dialysis experiment using a 1:2 ratio of rhGH:GHBP peptides.

This experiment was carried out according to the method in Example 2 except that the rhGH: peptide ratio was 1:2. Standard curves for peptides 1-5, 6-10, and 10 alone, are shown in FIGS. 9, 10 and 11, respectively. The results of this experiment are shown in FIG. 12. In the absence of rhGH, the concentration of each peptide in the lower chamber would have been 11.36 uM. As indicated, no reduction of the concentration of any of the peptides in the lower chamber was observed in the presence of rhGH at a 1:2 ratio of rhGH; peptide.

---

What is claimed is:

1. A polypeptide that binds to growth hormone, wherein the polypeptide comprises a peptide comprising the peptide of SEQ ID NO: 5 or the corresponding amino acid sequence from a non-human primate, a horse, a pig, a cow, a sheep, a chicken, a dog, a cat, a rat, a mouse, or a rabbit growth hormone receptor; and the peptide of SEQ ID NO: 6 or the corresponding amino acid sequence from a non-human primate, a horse, a pig, a cow, a sheep, a chicken, a dog, a cat, a rat, a mouse, or a rabbit growth hormone receptor; and wherein the SEQ ID NO: 5, or the corresponding amino acid sequence from a non-human primate, horse, pig, cow, sheep, chicken, dog, cat, rat, mouse or rabbit growth hormone receptor and SEQ ID NO: 6 or the corresponding amino acid sequence from a non-human primate, horse, pig, cow, sheep, chicken, dog, cat, rat, mouse or rabbit growth hormone receptor; are bridged by the peptide YCIGKCFS (amino acids 7-14 of SEQ ID NO: 7) or YGS; and wherein the polypeptide has a sequence that differs from a wild-type fragment of a GHBP from a human, non-human primate, horse, pig, cow, sheep, chicken, dog, cat, rat, mouse, or rabbit growth hormone receptor.

2. The polypeptide of claim 1 wherein the polypeptide consists of an amino acid sequence selected from the group consisting SEQ ID NO: 7 and SEQ ID NO: 8.

3. A pharmaceutical composition comprising a therapeutic effective amount of any one of the polypeptides of claim 1 and a pharmaceutically acceptable carrier or excipient.

4. The pharmaceutical composition of claim 3, comprising a pharmaceutically acceptable excipient selected from the group consisting of a buffer, a preservative, a lubricating agent, a wetting agents, an emulsifying agent, a suspending agent, a sweetening agent, and a flavoring agent.

5. A substantially pure polypeptide that binds to growth hormone, wherein the polypeptide comprises SEQ ID NO: 5 or the corresponding amino acid sequence from a non-human primate, a horse, a pig, a cow, a sheep, a chicken a dog, a cat, a rat, a mouse, or a rabbit growth hormone receptor; and the peptide of SEQ ID NO: 6 or the corresponding amino acid sequence from a non-human primate, a horse, a pig, a cow, a sheep, a chicken, a dog, a cat, a rat, a mouse, or a rabbit growth hormone receptor, wherein the SEQ ID NO: 5, or the corresponding amino acid sequence from a non-human primate, horse, pig, cow, sheep, chicken, dog, cat, rat, mouse or rabbit growth hormone receptor and SEQ ID NO: 6 or, the corresponding amino acid sequence from a non-human primate, horse, pig, cow, sheep, chicken, dog, cat, rat, mouse or rabbit growth hormone receptor are bridged by the peptide YCIGKCFS (amino acids 7-14 of SEQ ID NO: 7) or YGS; and wherein the polypeptide has a sequence that differs from a wild-type fragment of a GHBP from a human, non-human primate, horse, pig, cow, sheep, chicken, dog, cat, rat, mouse, or rabbit growth hormone receptor, wherein the polypeptide is selected from a chemically synthesized polypeptide or a recombinant polypeptide, wherein the polypeptide and has a sequence that differs from a wild-type fragment of a GHBP, and wherein the polypeptide is covalently or non-covalently bound to a larger carrier protein.

6. The substantially pure polypeptide of claim 5 wherein the peptide consists of an amino acid sequence of sequence selected from the group consisting of SEQ ID NO: 7 and SEQ ID NO: 8.

7. A pharmaceutical composition comprising a therapeutic effective amount of a substantially pure polypeptide of claim 5 and a pharmaceutically acceptable excipient, wherein the pharmaceutically acceptable excipient is selected from the group consisting of a buffer, a preservative, a lubricating agent, a wetting agents, an emulsifying agent, a suspending agent, a sweetening agent, and a flavoring agent, wherein the substantially pure polypeptide is lyophilized.

8. The pharmaceutical composition of claim 7, further comprising a pharmaceutically acceptable carrier or excipient.

9. The pharmaceutical composition of claim 3 or claim 8, wherein the pharmaceutically acceptable carrier comprises a liposome, a nanoparticle or a carrier protein.

10. The pharmaceutical composition of claim 9, further comprising a growth hormone polypeptide or fragment thereof.

11. The pharmaceutical composition of claim 10, wherein the growth hormone polypeptide is recombinant.

12. The pharmaceutical composition of claim 6, wherein the growth hormone polypeptide is human growth hormone.

13. A pharmaceutical composition comprising:

(a) a therapeutic effective amount of a polypeptide that binds to growth hormone, wherein the polypeptide comprises:

(i) SEQ ID NO: 5 or the corresponding amino acid sequence from a non-human primate, a horse, a pig, a cow, a sheep, a chicken, a dog, a cat, a rat, a mouse, or a rabbit growth hormone receptor; and (ii) the peptide of SEQ ID NO: 6 or the corresponding amino acid sequence from a non-human primate, a horse, a pig, a cow, a sheep, a chicken, a dog, a cat, a rat, a mouse, or a rabbit growth hormone receptor;

wherein the SEQ ID NO: 5, or the corresponding amino acid sequence from a non-human primate, horse, pig, cow, sheep, chicken, dog, cat, rat, mouse or rabbit growth hormone receptor and SEQ ID NO: 6 or, the corresponding amino acid sequence from a non-human primate, horse, pig, cow, sheep, chicken, dog, cat, rat, mouse or rabbit growth hormone receptor are bridged by the peptide YCIGKCFS (amino acids 7-14 of SEQ ID NO: 7) or YGS; and (b) a pharmaceutically acceptable excipient,
wherein the polypeptide and has a sequence that differs from a wild-type fragment of a GHBP from a human, non-human primate, horse, pig, cow, sheep, chicken, dog, cat, rat, mouse, or rabbit growth hormone receptor.

14. The pharmaceutical composition of claim 13, wherein the peptide consists of an amino acid sequence of sequence selected from the group consisting of SEQ ID NO: 7 and SEQ ID NO: 8.

* * * * *

SEQUENCE LISTING

```
<160> NUMBER OF SEQ ID NOS: 14

<210> SEQ ID NO 1
<211> LENGTH: 8
<212> TYPE: PRT
<213> ORGANISM: Homo sapiens

<400> SEQUENCE: 1

Ser Pro Glu Arg Glu Thr Phe Ser
1               5

<210> SEQ ID NO 2
<211> LENGTH: 13
<212> TYPE: PRT
<213> ORGANISM: Homo sapiens

<400> SEQUENCE: 2

Arg Arg Asn Thr Gln Glu Trp Thr Gln Glu Trp Lys Glu
1               5                   10

<210> SEQ ID NO 3
<211> LENGTH: 6
<212> TYPE: PRT
<213> ORGANISM: Homo sapiens

<400> SEQUENCE: 3

Arg Arg Asn Thr Gln Glu
```

1          5

<210> SEQ ID NO 4
<211> LENGTH: 7
<212> TYPE: PRT
<213> ORGANISM: Homo sapiens

<400> SEQUENCE: 4

Trp Thr Gln Glu Trp Lys Glu
1               5

<210> SEQ ID NO 5
<211> LENGTH: 6
<212> TYPE: PRT
<213> ORGANISM: Homo sapiens

<400> SEQUENCE: 5

Thr Ser Ile Trp Ile Pro
1               5

<210> SEQ ID NO 6
<211> LENGTH: 8
<212> TYPE: PRT
<213> ORGANISM: Homo sapiens

<400> SEQUENCE: 6

Val Asp Glu Ile Val Gln Pro Asp
1               5

<210> SEQ ID NO 7
<211> LENGTH: 22
<212> TYPE: PRT
<213> ORGANISM: Homo sapiens

<400> SEQUENCE: 7

Thr Ser Ile Trp Ile Pro Tyr Cys Ile Gly Lys Cys Phe Ser Val Asp
1               5                   10                  15

Glu Ile Val Gln Pro Asp
            20

<210> SEQ ID NO 8
<211> LENGTH: 17
<212> TYPE: PRT
<213> ORGANISM: Homo sapiens

<400> SEQUENCE: 8

Thr Ser Ile Trp Ile Pro Tyr Gly Ser Val Asp Glu Ile Val Gln Pro
1               5                   10                  15

Asp

<210> SEQ ID NO 9
<211> LENGTH: 7
<212> TYPE: PRT
<213> ORGANISM: Homo sapiens

<400> SEQUENCE: 9

Lys Val Asp Lys Glu Tyr Glu
1               5

<210> SEQ ID NO 10
<211> LENGTH: 7
<212> TYPE: PRT
<213> ORGANISM: Homo sapiens

<400> SEQUENCE: 10

Arg Val Arg Ser Lys Gln Arg
1               5

<210> SEQ ID NO 11
<211> LENGTH: 238
<212> TYPE: PRT
<213> ORGANISM: Homo sapiens

<400> SEQUENCE: 11

Phe Ser Gly Ser Glu Ala Thr Ala Ala Ile Leu Ser Arg Ala Pro Trp
1               5                   10                  15

Ser Leu Gln Ser Val Asn Pro Gly Leu Lys Thr Asn Ser Ser Lys Glu
                20                  25                  30

Pro Lys Phe Thr Lys Cys Arg Ser Pro Glu Arg Glu Thr Phe Ser Cys
            35                  40                  45

His Trp Thr Asp Glu Val His His Gly Thr Lys Asn Leu Gly Pro Ile
        50                  55                  60

Gln Leu Phe Tyr Thr Arg Arg Asn Thr Gln Glu Trp Thr Gln Glu Trp
65                  70                  75                  80

Lys Glu Cys Pro Asp Tyr Val Ser Ala Gly Glu Asn Ser Cys Tyr Phe
                85                  90                  95

Asn Ser Ser Phe Thr Ser Ile Trp Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Pro Ile Ala Leu Asn Trp Thr Leu Leu Asn Val
130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205

Glu Val Arg Val Arg Ser Lys Gln Arg Asn Ser Gly Asn Tyr Gly Glu
    210                 215                 220

Phe Ser Glu Val Leu Tyr Val Thr Leu Pro Gln Met Ser Gln
225                 230                 235

<210> SEQ ID NO 12
<211> LENGTH: 638
<212> TYPE: PRT
<213> ORGANISM: Homo sapiens

<400> SEQUENCE: 12

Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
                20                  25                  30

Pro Trp Ser Leu Gln Ser Val Asn Pro Gly Leu Lys Thr Asn Ser Ser
            35                  40                  45

Lys Glu Pro Lys Phe Thr Lys Cys Arg Ser Pro Glu Arg Glu Thr Phe
        50                  55                  60

Ser Cys His Trp Thr Asp Glu Val His His Gly Thr Lys Asn Leu Gly

```
                65                  70                  75                  80
        Pro Ile Gln Leu Phe Tyr Thr Arg Arg Asn Thr Gln Glu Trp Thr Gln
                            85                  90                  95
        Glu Trp Lys Glu Cys Pro Asp Tyr Val Ser Ala Gly Glu Asn Ser Cys
                        100                 105                 110
        Tyr Phe Asn Ser Ser Phe Thr Ser Ile Trp Ile Pro Tyr Cys Ile Lys
                    115                 120                 125
        Leu Thr Ser Asn Gly Gly Thr Val Asp Glu Lys Cys Phe Ser Val Asp
                130                 135                 140
        Glu Ile Val Gln Pro Asp Pro Ile Ala Leu Asn Trp Thr Leu Leu
        145                 150                 155                 160
        Asn Val Ser Leu Thr Gly Ile His Ala Asp Ile Gln Val Arg Trp Glu
                            165                 170                 175
        Ala Pro Arg Asn Ala Asp Ile Gln Lys Gly Trp Met Val Leu Glu Tyr
                        180                 185                 190
        Glu Leu Gln Tyr Lys Glu Val Asn Glu Thr Lys Trp Lys Met Met Asp
                    195                 200                 205
        Pro Ile Leu Thr Thr Ser Val Pro Val Tyr Ser Leu Lys Val Asp Lys
                210                 215                 220
        Glu Tyr Glu Val Arg Val Arg Ser Lys Gln Arg Asn Ser Gly Asn Tyr
        225                 230                 235                 240
        Gly Glu Phe Ser Glu Val Leu Tyr Val Thr Leu Pro Gln Met Ser Gln
                            245                 250                 255
        Phe Thr Cys Glu Glu Asp Phe Tyr Phe Pro Trp Leu Leu Ile Ile Ile
                        260                 265                 270
        Phe Gly Ile Phe Gly Leu Thr Val Met Leu Phe Val Phe Leu Phe Ser
                    275                 280                 285
        Lys Gln Gln Arg Ile Lys Met Leu Ile Leu Pro Pro Val Pro Val Pro
                290                 295                 300
        Lys Ile Lys Gly Ile Asp Pro Asp Leu Leu Lys Glu Gly Lys Leu Glu
        305                 310                 315                 320
        Glu Val Asn Thr Ile Leu Ala Ile His Asp Ser Tyr Lys Pro Glu Phe
                            325                 330                 335
        His Ser Asp Asp Ser Trp Val Glu Phe Ile Glu Leu Asp Ile Asp Glu
                        340                 345                 350
        Pro Asp Glu Lys Thr Glu Glu Ser Asp Thr Asp Arg Leu Leu Ser Ser
                    355                 360                 365
        Asp His Glu Lys Ser His Ser Asn Leu Gly Val Lys Asp Gly Asp Ser
                370                 375                 380
        Gly Arg Thr Ser Cys Cys Glu Pro Asp Ile Leu Glu Thr Asp Phe Asn
        385                 390                 395                 400
        Ala Asn Asp Ile His Glu Gly Thr Ser Glu Val Ala Gln Pro Gln Arg
                            405                 410                 415
        Leu Lys Gly Glu Ala Asp Leu Leu Cys Leu Asp Gln Lys Asn Gln Asn
                        420                 425                 430
        Asn Ser Pro Tyr His Asp Ala Cys Pro Ala Thr Gln Gln Pro Ser Val
                    435                 440                 445
        Ile Gln Ala Glu Lys Asn Lys Pro Gln Pro Leu Pro Thr Glu Gly Ala
                450                 455                 460
        Glu Ser Thr His Gln Ala Ala His Ile Gln Leu Ser Asn Pro Ser Ser
        465                 470                 475                 480
        Leu Ser Asn Ile Asp Phe Tyr Ala Gln Val Ser Asp Ile Thr Pro Ala
                            485                 490                 495
```

```
Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635
```

<210> SEQ ID NO 13
<211> LENGTH: 4563
<212> TYPE: DNA
<213> ORGANISM: Homo sapiens

<400> SEQUENCE: 13

```
cggcggcggc ggcggcagcg gcagcagcag ctgctacagt ggcggtggcg gcggcggctg      60
ctgctgagcc cggcggcgg cggggacccc gggctggggc cacgcgggcc ggaggccccg     120
gcaccattgg ccccagcgca gacgcgaacc cgcgctctct gatcagaggc gaagctcgga    180
ggtcctacag gtatggatct ctggcagctg ctgttgacct tggcactggc aggatcaagt    240
gatgctttt ctggaagtga ggccacagca gctatcctta gcagagcacc ctggagtctg     300
caaagtgtta atccaggcct aaagacaaat tcttctaagg agcctaaatt caccaagtgc    360
cgttcacctg agcgagagac ttttttcatgc cactggacag atgaggttca tcatggtaca    420
agaacctag acccataca gctgttctat accagaagga acactcaaga atggactcaa     480
gaatggaaag aatgccctga ttatgttct gctggggaaa acagctgtta ctttaattca     540
tcgtttacct ccatctggat accttattgt atcaagctaa ctagcaatgg tggtacagtg    600
gatgaaaagt gttctctgt tgatgaaata gtgcaaccag atccacccat tgccctcaac    660
tggactttac tgaacgtcag tttaactggg attcatgcag atatccaagt gagatgggaa    720
gcaccacgca atgcagatat tcagaaagga tggatggttc tggagtatga acttcaatac    780
aaagaagtaa atgaaactaa atggaaaatg atggacccta tattgacaac atcagttcca    840
gtgtactcat tgaaagtgga taaggaatat gaagtgcgtg tgagatccaa acaacgaaac    900
tctggaaatt atggcgagtt cagtgaggtg ctctatgtaa cacttcctca gatgagccaa    960
tttacatgtg aagaagattt ctactttcca tggctcttaa ttattatctt tggaatattt   1020
gggctaacag tgatgctatt tgtattctta ttttctaaac agcaaggat taaaatgctg    1080
attctgcccc cagttccagt tccaaagatt aaaggaatcg atccagatct cctcaaggaa   1140
ggaaaattag aggaggtgaa cacaatctta gccattcatg atagctataa acccgaattc   1200
cacagtgatg actcttgggt tgaatttatt gagctagata ttgatgagcc agatgaaaag   1260
actgaggaat cagacacaga cagacttcta agcagtgacc atgagaaatc acatagtaac   1320
```

```
ctaggggtga aggatggcga ctctggacgt accagctgtt gtgaacctga cattctggag    1380
actgatttca atgccaatga catacatgag ggtacctcag aggttgctca gccacagagg    1440
ttaaaagggg aagcagatct cttatgcctt gaccagaaga atcaaaataa ctcaccttat    1500
catgatgctt gccctgctac tcagcagccc agtgttatcc aagcagagaa aaacaaacca    1560
caaccacttc ctactgaagg agctgagtca actcaccaag ctgcccatat tcagctaagc    1620
aatccaagtt cactgtcaaa catcgacttt tatgcccagg tgagcgacat tacaccagca    1680
ggtagtgtgg tccttttcccc gggccaaaag aataaggcag ggatgtccca atgtgacatg    1740
cacccggaaa tggtctcact ctgccaagaa aacttcctta tggacaatgc ctacttctgt    1800
gaggcagatg ccaaaaagtg catccctgtg gctcctcaca tcaaggttga atcacacata    1860
cagccaagct taaaccaaga ggacatttac atcaccacag aaagcctttac cactgctgct    1920 gggaggcctg gacaggaga acatgttcca ggttctgaga tgcctgtccc agactatacc    1980
tccattcata tagtacagtc cccacagggc ctcatactca atgcgactgc cttgcccttg    2040
cctgacaaag agtttctctc atcatgtggc tatgtgagca cagaccaact gaacaaaatc    2100
atgccttagc cttctttgg tttcccaaga gctacgtatt aatagcaaa gaattgactg    2160 gggcaataac gtttaagcca aaacaatgtt taaaccttt ttggggagt gacaggatgg    2220 ggtatggatt ctaaaatgcc ttttcccaaa atgttgaaat atgatgttaa aaaaataaga    2280
agaatgctta atcagataga tattcctatt gtgcaatgta aatattttaa agaattgtgt    2340
cagactgttt agtagcagtg attgtcttaa tattgtgggt gttaattttt gatactaagc    2400
attgaatggc tatgttttta atgtatagta aatcacgctt tttgaaaaag cgaaaaaatc    2460
aggtggcttt tgcggttcag gaaaattgaa tgcaaaccat agcacaggct aattttttgt    2520
tgtttcttaa ataagaaact tttttattta aaaaactaaa aactagaggt gagaaattta    2580
aactataagc aagaaggcaa aaatagtttg gatatgtaaa acatttattt tgacataaag    2640
ttgataaaga tttttttaata atttagactt caagcatggc tattttatat tacactacac    2700
actgtgtact gcagttggta tgaccccctct aaggagtgta gcaactacag tctaaagctg    2760
gtttaatgtt ttggccaatg cacctaaaga aaaacaaact cgttttttac aaagcccttt    2820
tatacctccc cagactcctt caacaattct aaaatgattg tagtaatctg cattattgga    2880
atataattgt tttatctgaa ttttttaaaca agtatttgtt aatttagaaa actttaaagc    2940
gtttgcacag atcaacttac caggcaccaa aagaagtaaa agcaaaaaag aaaacctttc    3000
ttcaccaaat cttggttgat gccaaaaaaa aatacatgct aagagaagta gaaatcatag    3060
ctggttcaca ctgaccaaga tacttaagtg ctgcaattgc acgcggagtg agttttttag    3120
tgcgtgcaga tggtgagaga taagatctat agcctctgca gcggaatctg ttcacaccca    3180
acttggtttt gctacataat tatccaggaa gggaataagg tacaagaagc attttgtaag    3240
ttgaagcaaa tcgaatgaaa ttaactgggt aatgaaacaa agagttcaag aaataagttt    3300
ttgtttcaca gcctataacc agacacatac tcatttttca tgataatgaa cagaacatag    3360
acagaagaaa caaggttttc agtccccaca gataactgaa aattatttaa accgctaaaa    3420
gaaactttct ttctcactaa atcttttata ggatttattt aaaatagcaa aagaagaagt    3480
ttcatcattt tttacttcct ctctgagtgg actggcctca aagcaagcat tcagaagaaa    3540
aagaagcaac ctcagtaatt tagaaatcat tttgcaatcc cttaatatcc taaacatcat    3600
tcatttttgt tgttgttgtt gttgttgaga cagagtctcg ctctgtcgcc aggctagagt    3660
```

```
gcggtggcgc gatcttgact cactgcaatc tccacctccc acaggttcag gcgattcccg    3720
tgcctcagcc tcctgagtag ctgggactac aggcacgcac caccatgcca ggctaatttt    3780
tttgtatttt agcagagacg gggtttcacc atgttggcca ggatggtctc gatctcctga    3840
cctcgtgatc cacccgactc ggcctcccaa agtgctggga ttacaggtgt aagccaccgt    3900
gcccagccct aaacatcatt cttgagagca ttgggatatc tcctgaaaag gtttatgaaa    3960
aagaagaatc tcatctcagt gaagaatact tctcattttt taaaaaagct taaaactttg    4020
aagttagctt taacttaaat agtatttccc atttatcgca gaccttttt aggaagcaag     4080 cttaatggct gataatttta aattctctct cttgcaggaa ggactatgaa aagctagaat    4140
tgagtgttta aagttcaaca tgttatttgt aatagatgtt tgatagattt tctgctactt    4200
tgctgctatg gttttctcca agagctacat aatttagttt catataaagt atcatcagtg    4260
tagaacctaa ttcaattcaa agctgtgtgt ttggaagact atcttactat ttcacaacag    4320
cctgacaaca tttctatagc caaaaatagc taaatacctc aatcagtctc agaatgtcat    4380
tttggtactt tggtggccac ataagccatt attcactagt atgactagtt gtgtctggca    4440
gtttatattt aactctcttt atgtctgtgg attttttcct tcaaagttta ataaatttat    4500
tttcttggat tcctgatagt gtgcttctgt tatcaaacac caacataaaa atgatctaaa    4560
cca                                                                  4563
```

<210> SEQ ID NO 14
<211> LENGTH: 246
<212> TYPE: PRT
<213> ORGANISM: Homo sapiens

<400> SEQUENCE: 14

Ala Leu Ala Gly Ser Ser Asp Ala Phe Ser Gly Ser Glu Ala Thr Ala
1               5                   10                  15

Ala Ile Leu Ser Arg Ala Pro Trp Ser Leu Gln Ser Val Asn Pro Gly
            20                  25                  30

Leu Lys Thr Asn Ser Ser Lys Glu Pro Lys Phe Thr Lys Cys Arg Ser
        35                  40                  45

Pro Glu Arg Glu Thr Phe Ser Cys His Trp Thr Asp Glu Val His His
    50                  55                  60

Gly Thr Lys Asn Leu Gly Pro Ile Gln Leu Phe Tyr Thr Arg Arg Asn
65                  70                  75                  80

Thr Gln Glu Trp Thr Gln Glu Trp Lys Glu Cys Pro Asp Tyr Val Ser
                85                  90                  95

Ala Gly Glu Asn Ser Cys Tyr Phe Asn Ser Ser Phe Thr Ser Ile Trp
            100                 105                 110

Ile Pro Tyr Cys Ile Lys Leu Thr Ser Asn Gly Gly Thr Val Asp Glu
        115                 120                 125

Lys Cys Phe Ser Val Asp Glu Ile Val Gln Pro Asp Pro Pro Ile Ala
    130                 135                 140

Leu Asn Trp Thr Leu Leu Asn Val Ser Leu Thr Gly Ile His Ala Asp
145                 150                 155                 160

Ile Gln Val Arg Trp Glu Ala Pro Arg Asn Ala Asp Ile Gln Lys Gly
                165                 170                 175

Trp Met Val Leu Glu Tyr Glu Leu Gln Tyr Lys Glu Val Asn Glu Thr
            180                 185                 190

Lys Trp Lys Met Met Asp Pro Ile Leu Thr Thr Ser Val Pro Val Tyr
        195                 200                 205

-continued

```
Ser Leu Lys Val Asp Lys Glu Tyr Glu Val Arg Val Arg Ser Lys Gln
    210             215             220
Arg Asn Ser Gly Asn Tyr Gly Glu Phe Ser Glu Val Leu Tyr Val Thr
225             230             235             240
Leu Pro Gln Met Ser Gln
                245
```